(12) United States Patent
Bilotta et al.

(10) Patent No.: US 9,511,059 B2
(45) Date of Patent: Dec. 6, 2016

(54) ANTIVIRAL COMPOUNDS

(71) Applicant: Hoffmann-La Roche Inc., Nutley, NJ (US)

(72) Inventors: Joseph Anthony Bilotta, Nutley, NJ (US); Zhi Chen, Livingston, NJ (US); Qingjie Ding, Bridgewater, NJ (US); Shawn David Erickson, Leonia, NJ (US); Eric Mertz, Fair Lawn, NJ (US); Robert James Weikert, Basel (CH)

(73) Assignee: HOFFMANN-LA ROCHE INC., Nutley, NJ (US)

(*) Notice: Subject to any disclaimer, the term of this patent is extended or adjusted under 35 U.S.C. 154(b) by 0 days.

(21) Appl. No.: 14/827,762

(22) Filed: Aug. 17, 2015

(65) Prior Publication Data

US 2015/0353511 A1 Dec. 10, 2015

Related U.S. Application Data

(63) Continuation of application No. 14/159,566, filed on Jan. 21, 2014, now abandoned.

(60) Provisional application No. 61/755,519, filed on Jan. 23, 2013.

(51) Int. Cl.
C07D 249/14 (2006.01)
C07D 401/12 (2006.01)
A61K 31/4439 (2006.01)
A61K 31/4196 (2006.01)
A61K 45/06 (2006.01)

(52) U.S. Cl.
CPC ....... A61K 31/4439 (2013.01); A61K 31/4196 (2013.01); A61K 45/06 (2013.01); C07D 249/14 (2013.01); C07D 401/12 (2013.01)

(58) Field of Classification Search
None
See application file for complete search history.

(56) References Cited

U.S. PATENT DOCUMENTS

2004/0186288 A1 9/2004 Kruger et al.
2014/0010783 A1* 1/2014 Bilotta ................. C07D 249/14
424/85.4

FOREIGN PATENT DOCUMENTS

WO  2007030680     3/2007
WO  WO 2014/006066 * 1/2014 ........... C07D 249/14

OTHER PUBLICATIONS

The Japanese Office Action, issued on Jul. 14, 2016, in the corresponding Japanese Application No. 2015-554113.
The Chinese Office Action, issued on Aug. 3, 2016, in the corresponding Chinese Application No. 201480005630.6.

* cited by examiner

Primary Examiner — Alicia L Otton

(57) ABSTRACT

The present invention discloses compounds of Formula I:

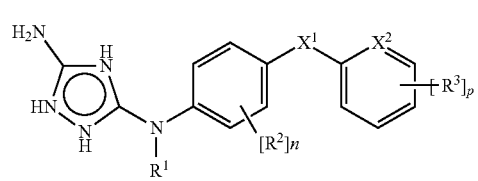

wherein the variables in Formula I are defined as described herein. Also disclosed are pharmaceutical compositions containing such compounds and methods for using the compounds of Formula I in the prevention or treatment of HCV infection.

1 Claim, No Drawings

ANTIVIRAL COMPOUNDS

This application is a Continuation of pending U.S. application Ser. No. 14/159,566, filed Jan. 21, 2014, which in turn, which in turn claims the benefit of U.S. Provisional Patent Application Ser. No. 61/755,519, filed Jan. 23, 2013, all of which are hereby incorporated by references in their entireties.

FIELD OF THE INVENTION

Hepatitis C virus (HCV) infection is a major health problem that affects 170 million people worldwide and 3-4 million people in the United States (Armstrong, G. L., et al., Ann. Intern. Med. 2006, 144:705-714; Lauer, G. M., et al., N. Eng. J. Med. 2001, 345:41-52). HCV infection leads to chronic liver disease, such as cirrhosis and hepatocellular carcinoma in a substantial number of infected individuals. Chronic HCV infection associated liver cirrhosis and hepatocellular carcinoma are also the leading cause of liver transplantation in the United States. Current treatments for HCV infection include immunotherapy with pegylated interferon-α in combination with the nucleoside-analog ribavirin. Pegylated interferon-α in combination with ribavirin and one of the two recently approved HCV NS3 protease inhibitors Incivek or Victrelis is the current standard of care for the treatment of genotype 1 HCV infected patients, the most difficult to treat patient population. However, current HCV treatments are compromised by suboptimal sustained virological response rates and associated with severe side effects, as well as resistance to the protease inhibitors. Therefore there is a clear need for improved antiviral drugs with better efficacy, safety, and resistance profiles.

The infection of human hepatocytes by HCV, also known as HCV entry, is mediated by the functional interactions of virally-encoded envelope glycoproteins E1 and E2 and host cell co-receptors, followed by a receptor-mediated endocytosis processes. This HCV entry step is a putative target for therapeutic intervention. Several virally-encoded enzymes are also putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

Systems have been developed to study the biology of HCV entry into host cells. Pseudotyping systems where the E1 and E2 glycoproteins are used to functionally replace the glycoproteins of retroviruses have been developed (Bartosch, B., Dubuisson, J. and Cosset, F.-L. J. Exp. Med. 2003, 197:633-642; Hsu, M. et al. Proc. Natl. Acad. Sci. USA. 2003, 100:7271-7276). These systems yield HCV pseudoparticles that bind to and enter host cells in a manner which is believed to be analogous to the natural virus, thus making them a convenient tool to study the viral entry steps as well as to identify inhibitors blocking this process.

There is a clear and long-felt need to develop effective therapeutics for treatment of HCV infection. Specifically, there is a need to develop compounds that selectively inhibit HCV viral entry and replication and that are useful for treating HCV-infected patients and protecting liver transplant patients from HCV re-infection. This application discloses novel compounds that are effective in prevention of HCV infection. Additionally, the disclosed compounds provide advantages for pharmaceutical uses, for example, with respect to their mechanism of action, binding, prevention of infection, inhibition efficacy, and target selectivity.

SUMMARY OF THE INVENTION

The application provides compound of formula I

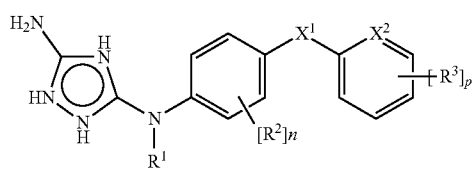

wherein:
$R^1$ is H or lower alkyl;
each $R^2$ is independently halo or lower haloalkyl;
n is 0, 1, or 2;
$R^3$ is lower haloalkyl, cyano, lower alkoxy, $C(=O)OCH_3$, or $S(=O)_2CH_3$;
p is 0, or 1;
$X^1$ is S, $S(=O)_2$, O, $S(=O)$, NH, or $OCH_2$; and
$X^2$ is CH or N;
or a pharmaceutically acceptable salt thereof.

The application provides a method for preventing a Hepatitis C Virus (HCV) infection comprising administering to a patient in need thereof a therapeutically effective amount of a compound of Formula I.

The application provides a method for treating a Hepatitis C Virus (HCV) infection comprising administering to a patient in need thereof a therapeutically effective amount of a compound of Formula I.

The application provides a composition comprising a compound of Formula I and a pharmaceutically acceptable excipient.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

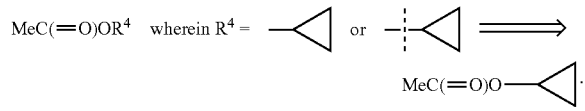

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

If a substituent is designated to be "absent", the substituent is not present.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "carbonyl" or "acyl" as used herein denotes a group of formula —C(=O)R wherein R is hydrogen or lower alkyl as defined herein.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "haloalkoxy" or "halo lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The term "sulfinyl" as used herein denotes a —SO— group.

The term "sulfonyl" as used herein denotes a —SO$_2$— group.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The term "lower alkyl sulfonylamido" as used herein refers to a group of formula —S(=O)$_2$NR$_2$ wherein each R is independently hydrogen or C$_{1-3}$ alkyl, and lower alkyl is as defined herein.

The term "trifluoromethyl sulfonyl" as used herein refers to a group of formula —S(=O)$_2$CF$_3$.

The term "trifluoromethyl sulfinyl" as used herein refers to a group of formula —S(=O)CF$_3$.

The term "trifluoromethyl sulfanyl" as used herein refers to a group of formula —SCF$_3$.

The term "nitro" as used herein refers to a group of formula —N$^+$(=O)O$^-$.

The term "carboxyl" as used herein refers to a group of formula —C(=O)R$_2$ wherein each R is independently hydrogen or C$_{1-3}$ alkyl, and lower alkyl is as defined herein.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "amino" as used herein denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "amido" as used herein denotes a group of the formula —C(=O)NR'R" or —NR'C(=O)R" wherein R' and R" are independently hydrogen, alkyl, alkoxy, cycloalkyl, heterocycloalkyl, aryl or heteroaryl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

Inhibitors of HCV Entry

The application provides a compound of formula I

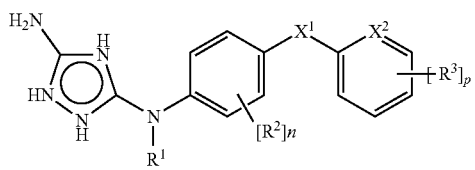

wherein:
R$^1$ is H or lower alkyl;
each R$^2$ is independently halo or lower haloalkyl;
n is 0, 1, or 2;
R$^3$ is lower haloalkyl, cyano, lower alkoxy, C(=O)OCH$_3$, or S(=O)$_2$CH$_3$;
p is 0, or 1;

$X^1$ is S, S(=O)$_2$, O, S(=O), NH, or OCH$_2$; and
$X^2$ is CH or N;
or a pharmaceutically acceptable salt thereof.

The application provides a compound of formula I, wherein $X^2$ is CH and $R^1$ is H.

The application provides a compound of formula I, wherein $X^1$ is S or O.

The application provides a compound of formula I, wherein $X^1$ is S(=O)$_2$ or S(=O).

The application provides a compound of formula I, wherein $X^1$ is S or O, $X^2$ is CH and $R^1$ is H.

The application provides a compound of formula I, wherein $X^1$ is S(=O)$_2$ or S(=O), $X^2$ is CH and $R^1$ is H.

The application provides any of the above compounds of formula I, wherein n 1.

The application provides the above compound of formula I, wherein $R^1$ is Cl.

The application provides any of the above compounds of formula I, wherein n is 2.

The application provides the above compound of formula I, wherein both $R^1$ are Cl.

The application provides any of the above compounds of formula I, wherein p is 0.

The application provides any of the above compounds of formula I, wherein p is 1.

The application provides any of the above compounds of formula I, wherein $R^3$ is or S(=O)$_2$CH$_3$, cyano, or CF$_3$.

The application provides a compound selected from the group consisting of:
N5-(3-Fluoro-4-phenylsulfanyl-5-trifluoromethyl-phenyl)-1H-[1,2,4]triazole-3,5-diamine;
N3-(3-Chloro-4-phenylamino-phenyl)-1H-[1,2,4]triazole-3,5-diamine;
N3-(3-Chloro-4-phenoxy-phenyl)-1H-[1,2,4]triazole-3,5-diamine;
N3-(3,5-Dichloro-4-phenylsulfanyl-phenyl)-1H-[1,2,4]triazole-3,5-diamine;
N3-(4-Benzenesulfinyl-3,5-dichloro-phenyl)-1H-[1,2,4]triazole-3,5-diamine;
N3-(4-Benzenesulfinyl-3,5-dichloro-phenyl)-1H-[1,2,4]triazole-3,5-diamine;
N3-[3,5-Dichloro-4-(4-trifluoromethyl-phenylsulfanyl)-phenyl]-1H-[1,2,4]triazole-3,5-diamine;
N3-[3,5-Dichloro-4-(4-trifluoromethyl-benzenesulfinyl)-phenyl]-1H-[1,2,4]triazole-3,5-diamine;
N3-[3,5-Dichloro-4-(4-trifluoromethyl-benzenesulfinyl)-phenyl]-1H-[1,2,4]triazole-3,5-diamine;
$N^3$-[3,5-Dichloro-4-(2-trifluoromethyl-phenylsulfanyl)-phenyl]-1H-[1,2,4]triazole-3,5-diamine;
$N^3$-[3,5-Dichloro-4-(3-trifluoromethyl-benzenesulfinyl)-phenyl]-1H-[1,2,4]triazole-3,5-diamine;
4-[4-(5-Amino-1H-[1,2,4]triazol-3-ylamino)-2,6-dichloro-phenylsulfanyl]-benzonitrile;
4-[4-(5-Amino-1H-[1,2,4]triazol-3-ylamino)-2,6-dichloro-benzenesulfinyl]-benzonitrile;
4-[4-(5-Amino-1H-[1,2,4]triazol-3-ylamino)-2,6-dichloro-benzenesulfonyl]-benzonitrile;
4-[4-(5-Amino-1H-[1,2,4]triazol-3-ylamino)-2-chloro-6-trifluoromethyl-phenylsulfanyl]-benzoic acid methyl ester;
$N^3$-[3,5-Dichloro-4-(4-methoxy-phenylsulfanyl)-phenyl]-1H-[1,2,4]triazole-3,5-diamine;
$N^3$-[3-Chloro-4-(4-methoxy-phenylsulfanyl)-5-trifluoromethyl-phenyl]-1H-[1,2,4]triazole-3,5-diamine;
$N^3$-[3,5-Dichloro-4-(4-methoxy-benzenesulfonyl)-phenyl]-1H-[1,2,4]triazole-3,5-diamine;
$N^3$-[3,5-Dichloro-4-(4-methanesulfonyl-phenoxy)-phenyl]-1H-[1,2,4]triazole-3,5-diamine;
$N^3$-[3-Chloro-4-(4-methanesulfonyl-phenoxy)-5-trifluoromethyl-phenyl]-1H-[1,2,4]triazole-3,5-diamine;
$N^3$-(3-Benzyloxy-5-chloro-phenyl)-1H-[1,2,4]triazole-3,5-diamine;
$N^3$-(3-Chloro-4-phenylsulfanyl-phenyl)-1H-[1,2,4]triazole-3,5-diamine;
$N^3$-(4-Benzenesulfonyl-3-chloro-phenyl)-1H-[1,2,4]triazole-3,5-diamine;
$N^3$-(3-Chloro-4-phenylsulfanyl-phenyl)-N-methyl-1H-[1,2,4]triazole-3,5-diamine;
$N^3$-(3-Chloro-5-phenoxy-phenyl)-1H-[1,2,4]triazole-3,5-diamine; and
$N^3$-[3,5-Dichloro-4-(pyridin-2-yloxy)-phenyl]-1H-[1,2,4]triazole-3,5-diamine.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering a combination of antiviral agents that inhibits replication of HCV.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

The application provides a composition comprising a compound of Formula I and a pharmaceutically acceptable excipient.

The application provides the use of the compound of Formula I in the preparation of a medicament for the prevention of HCV.

The application provides the use of the compound of Formula I in the preparation of a medicament for the treatment of HCV.

The application provides any compound, composition, method or use as described herein.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Table I depicts examples of compounds according to generic Formula I:

TABLE I

| # | Nomenclature | Structure |
|---|---|---|
| 1 | N5-(3-Fluoro-4-phenylsulfanyl-5-trifluoromethyl-phenyl)-1H-[1,2,4]triazole-3,5-diamine | 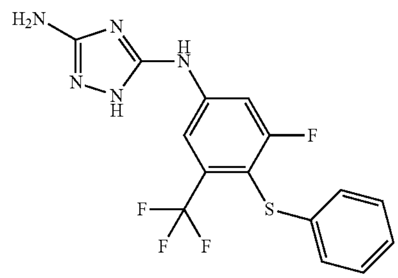 [SMILES: Nc1n[nH]c(Nc2cc(F)c(Sc3ccccc3)c(C(F)(F)F)c2)n1] |
| 2 | N3-(3-Chloro-4-phenylamino-phenyl)-1H-[1,2,4]triazole-3,5-diamine | 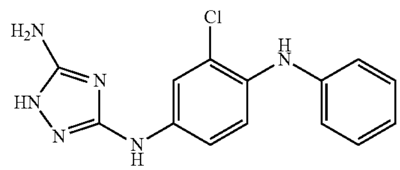 [SMILES: Nc1nc(Nc2ccc(Nc3ccccc3)c(Cl)c2)n[nH]1] |
| 3 | N3-(3-Chloro-4-phenoxy-phenyl)-1H-[1,2,4]triazole-3,5-diamine | 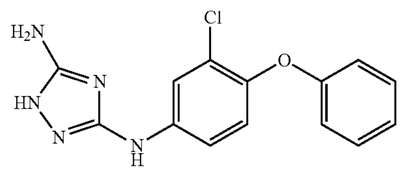 [SMILES: Nc1nc(Nc2ccc(Oc3ccccc3)c(Cl)c2)n[nH]1] |
| 4 | N3-(3,5-Dichloro-4-phenylsulfanyl-phenyl)-1H-[1,2,4]triazole-3,5-diamine | 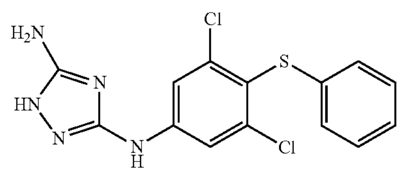 [SMILES: Nc1nc(Nc2cc(Cl)c(Sc3ccccc3)c(Cl)c2)n[nH]1] |
| 5 | N3-(4-Benzenesulfinyl-3,5-dichloro-phenyl)-1H-[1,2,4]triazole-3,5-diamine | 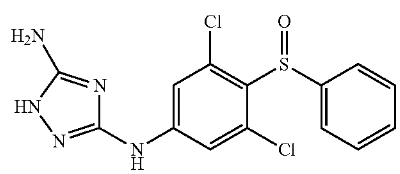 [SMILES: Nc1nc(Nc2cc(Cl)c(S(=O)c3ccccc3)c(Cl)c2)n[nH]1] |
| 6 | N3-(4-Benzenesulfinyl-3,5-dichloro-phenyl)-1H-[1,2,4]triazole-3,5-diamine | 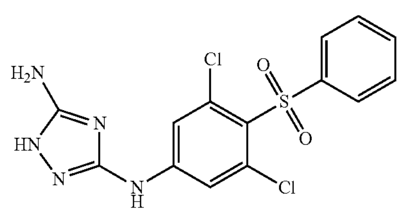 [SMILES: Nc1nc(Nc2cc(Cl)c(S(=O)(=O)c3ccccc3)c(Cl)c2)n[nH]1] |
| 7 | N3-[3,5-Dichloro-4-(4-trifluoromethyl-phenylsulfanyl)-phenyl]-1H-[1,2,4]triazole-3,5-diamine | 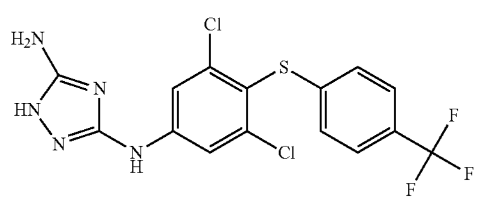 [SMILES: Nc1nc(Nc2cc(Cl)c(Sc3ccc(C(F)(F)F)cc3)c(Cl)c2)n[nH]1] |

TABLE I-continued

| # | Nomenclature | Structure |
|---|---|---|
| 8 | N3-[3,5-Dichloro-4-(4-trifluoromethyl-benzenesulfinyl)-phenyl]-1H-[1,2,4]triazole-3,5-diamine | 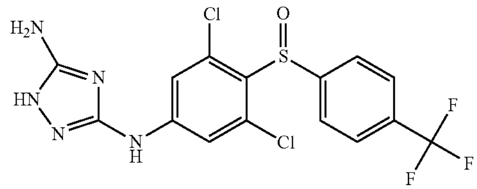 [SMILES: Nc1nc(Nc2cc(Cl)c(S(=O)c3ccc(C(F)(F)F)cc3)c(Cl)c2)n[nH]1] |
| 9 | N3-[3,5-Dichloro-4-(4-trifluoromethyl-benzenesulfinyl)-phenyl]-1H-[1,2,4]triazole-3,5-diamine | 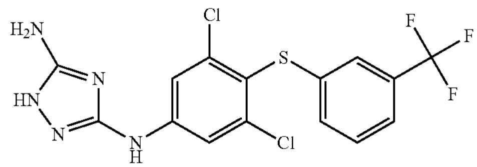 [SMILES: Nc1nc(Nc2cc(Cl)c(Sc3cccc(C(F)(F)F)c3)c(Cl)c2)n[nH]1] |
| 10 | $N^3$-[3,5-Dichloro-4-(2-trifluoromethyl-phenylsulfanyl)-phenyl]-1H-[1,2,4]triazole-3,5-diamine | 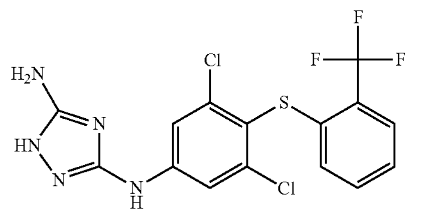 [SMILES: Nc1nc(Nc2cc(Cl)c(Sc3ccccc3C(F)(F)F)c(Cl)c2)n[nH]1] |
| 11 | $N^3$-[3,5-Dichloro-4-(3-trifluoromethyl-benzenesulfinyl)-phenyl]-1H-[1,2,4]triazole-3,5-diamine | 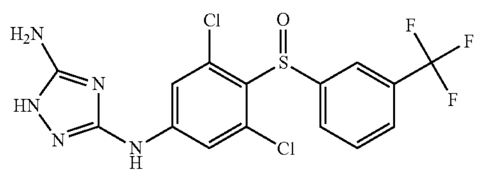 [SMILES: Nc1nc(Nc2cc(Cl)c(S(=O)c3cccc(C(F)(F)F)c3)c(Cl)c2)n[nH]1] |
| 12 | 4-[4-(5-Amino-1H-[1,2,4]triazol-3-ylamino)-2,6-dichloro-phenylsulfanyl]-benzonitrile | 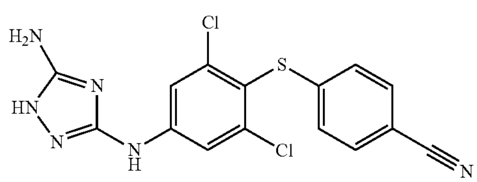 [SMILES: N#Cc1ccc(Sc2c(Cl)cc(Nc3n[nH]c(N)n3)cc2Cl)cc1] |
| 13 | 4-[4-(5-Amino-1H-[1,2,4]triazol-3-ylamino)-2,6-dichloro-benzenesulfinyl]-benzonitrile | 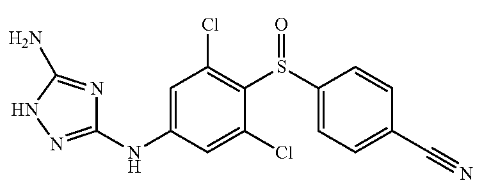 [SMILES: N#Cc1ccc(S(=O)c2c(Cl)cc(Nc3n[nH]c(N)n3)cc2Cl)cc1] |
| 14 | 4-[4-(5-Amino-1H-[1,2,4]triazol-3-ylamino)-2,6-dichloro-benzenesulfonyl]-benzonitrile | 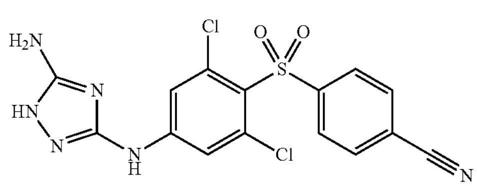 [SMILES: N#Cc1ccc(S(=O)(=O)c2c(Cl)cc(Nc3n[nH]c(N)n3)cc2Cl)cc1] |
| 15 | 4-[4-(5-Amino-1H-[1,2,4]triazol-3-ylamino)-2-chloro-6-trifluoromethyl-phenylsulfanyl]-benzoic acid methyl ester | 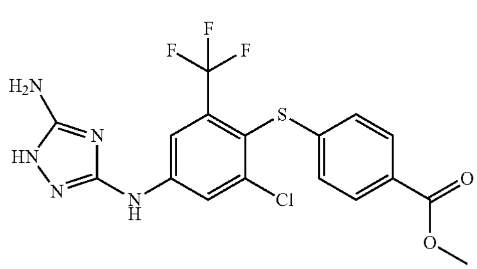 [SMILES: COC(=O)c1ccc(Sc2c(Cl)cc(Nc3n[nH]c(N)n3)cc2C(F)(F)F)cc1] |

TABLE I-continued

| # | Nomenclature | Structure |
|---|---|---|
| 16 | N³-[3,5-Dichloro-4-(4-methoxy-phenylsulfanyl)-phenyl]-1H-[1,2,4]triazole-3,5-diamine | 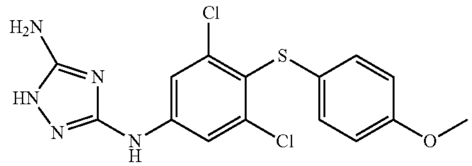 [SMILES: COc1ccc(Sc2c(Cl)cc(Nc3n[nH]c(N)n3)cc2Cl)cc1] |
| 17 | N³-[3-Chloro-4-(4-methoxy-phenylsulfanyl)-5-trifluoromethyl-phenyl]-1H-[1,2,4]triazole-3,5-diamine | 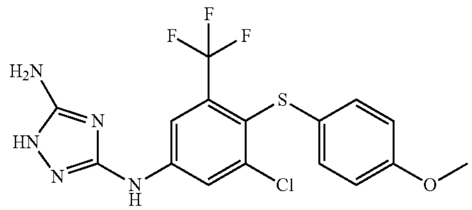 [SMILES: COc1ccc(Sc2c(Cl)cc(Nc3n[nH]c(N)n3)cc2C(F)(F)F)cc1] |
| 18 | N³-[3,5-Dichloro-4-(4-methoxy-benzenesulfonyl)-phenyl]-1H-[1,2,4]triazole-3,5-diamine | 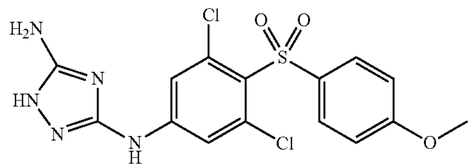 [SMILES: COc1ccc(S(=O)(=O)c2c(Cl)cc(Nc3n[nH]c(N)n3)cc2Cl)cc1] |
| 19 | N³-[3,5-Dichloro-4-(4-methanesulfonyl-phenoxy)-phenyl]-1H-[1,2,4]triazole-3,5-diamine | 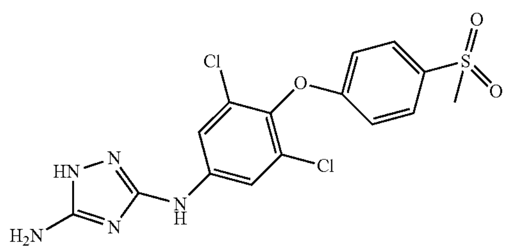 [SMILES: CS(=O)(=O)c1ccc(Oc2c(Cl)cc(Nc3n[nH]c(N)n3)cc2Cl)cc1] |
| 20 | N³-[3-Chloro-4-(4-methanesulfonyl-phenoxy)-5-trifluoromethyl-phenyl]-1H-[1,2,4]triazole-3,5-diamine | 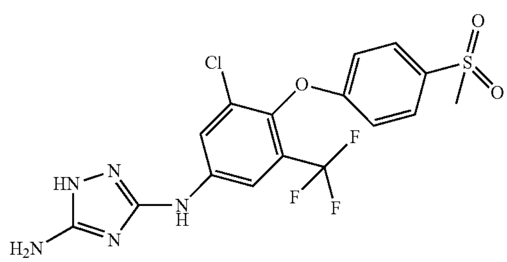 [SMILES: CS(=O)(=O)c1ccc(Oc2c(Cl)cc(Nc3n[nH]c(N)n3)cc2C(F)(F)F)cc1] |
| 21 | N³-(3-Benzyloxy-5-chloro-phenyl)-1H-[1,2,4]triazole-3,5-diamine | 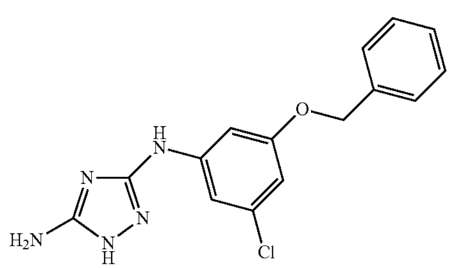 [SMILES: Nc1nc(Nc2cc(Cl)cc(OCc3ccccc3)c2)n[nH]1] |
| 22 | N³-(3-Chloro-4-phenylsulfanyl-phenyl)-1H-[1,2,4]triazole-3,5-diamine | 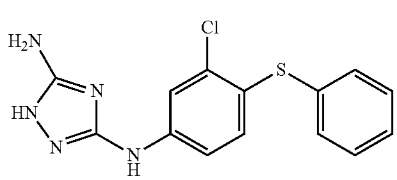 [SMILES: Nc1nc(Nc2ccc(Sc3ccccc3)c(Cl)c2)n[nH]1] |

TABLE I-continued

| # | Nomenclature | Structure |
|---|---|---|
| 23 | N³-(4-Benzenesulfonyl-3-chloro-phenyl)-1H-[1,2,4]triazole-3,5-diamine | 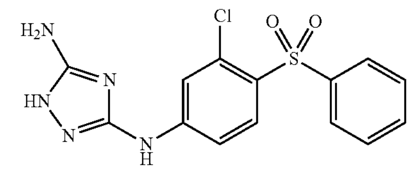 [SMILES: Nc1nc(Nc2ccc(S(=O)(=O)c3ccccc3)c(Cl)c2)n[nH]1] |
| 24 | N³-[3-Chloro-4-phenylsulfonyl-phenyl)-N³-methyl-1H-[1,2,4]triazole-3,5-diamine | 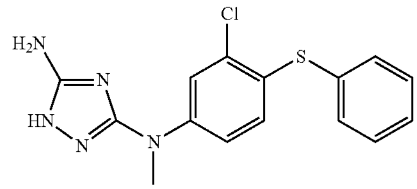 [SMILES: CN(c1ccc(Sc2ccccc2)c(Cl)c1)c1n[nH]c(N)n1] |
| 25 | N³-(3-Chloro-5-phenoxy-phenyl)-1H-[1,2,4]triazole-3,5-diamine | 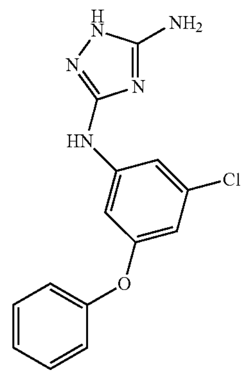 [SMILES: Nc1nc(Nc2cc(Cl)cc(Oc3ccccc3)c2)n[nH]1] |
| 26 | N³-[3,5-Dichloro-4-(pyridin-2-yloxy)-phenyl]-1H-[1,2,4]triazole-3,5-diamine | 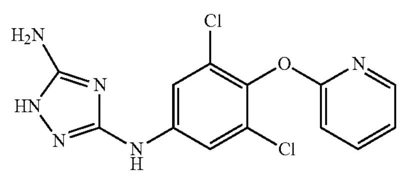 [SMILES: Nc1nc(Nc2cc(Cl)c(Oc3ccccn3)c(Cl)c2)n[nH]1] |

Synthesis
General Schemes
  The following schemes depict general methods for obtaining compounds of Formula
Procedure 1

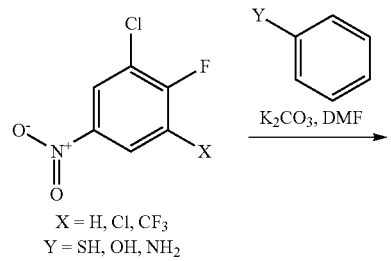

X = H, Cl, CF₃
Y = SH, OH, NH₂

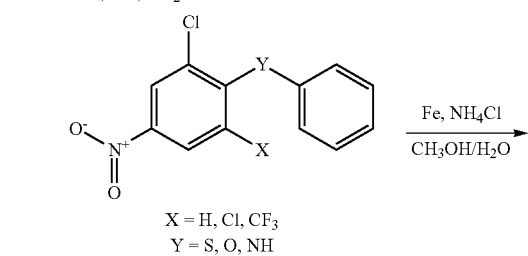

X = H, Cl, CF₃
Y = S, O, NH

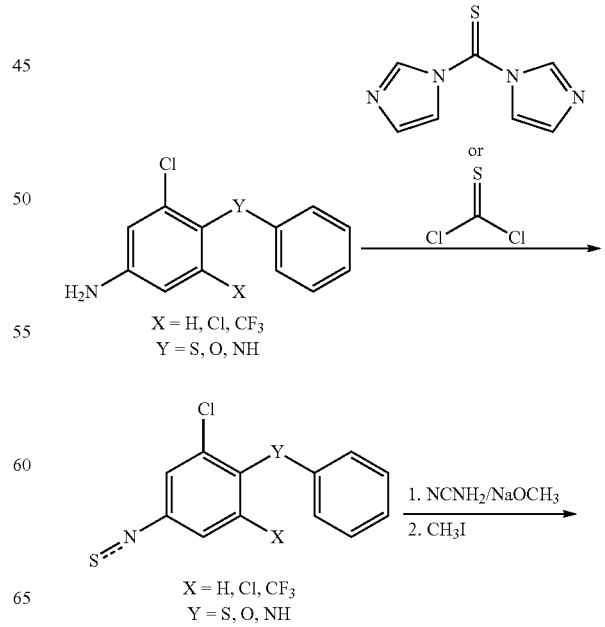

X = H, Cl, CF₃
Y = S, O, NH

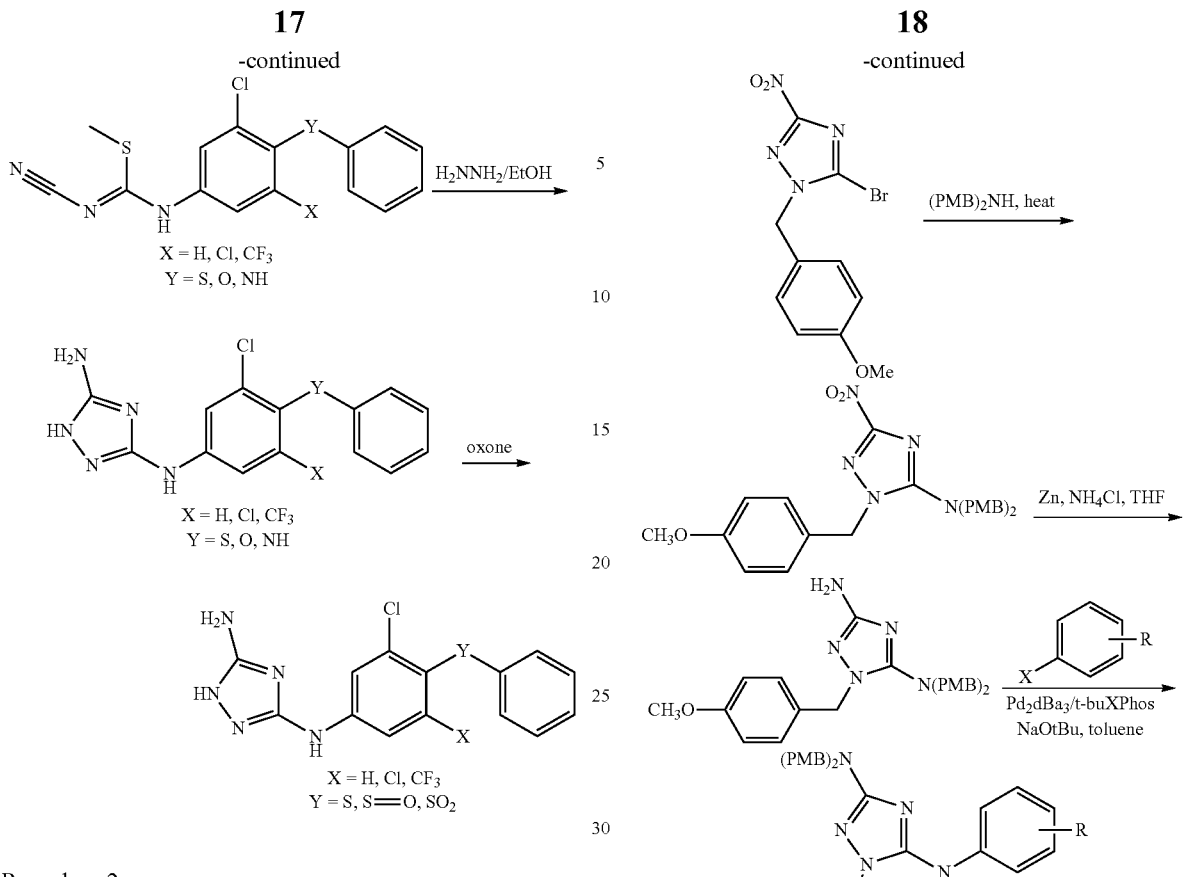

Procedure 2

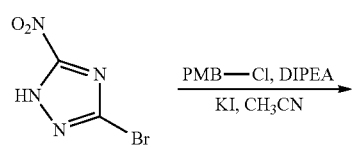

Procedure 3

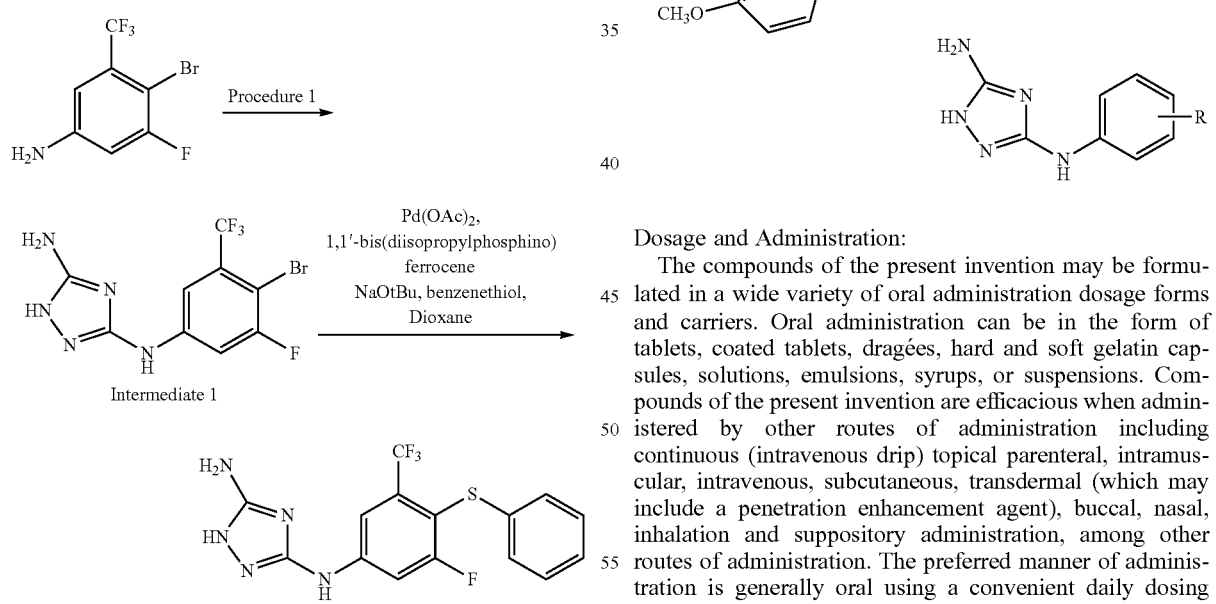

Dosage and Administration:

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment

Indications

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors, NS5A inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), micro-RNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/40381; WO00/56331, WO02/04425; WO03/007945; WO03/010141; WO03/000254; WO01/32153; WO00/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-$BuMe_2Si$ (TBDMS), tetra-n-butylammonium fluoride (TBAF), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

PREPARATIVE EXAMPLES

Intermediate 1

Procedure 1

$N^5$-(4-bromo-3-fluoro-5-trifluoromethylphenyl)-1H-[1,2,4]-triazole-3,5-diamine (Intermediate 3)

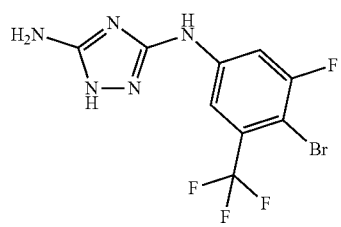 [SMILES: Nc1nc(Nc2cc(F)c(Br)c(C(F)(F)F)c2)n[nH]1]

2-bromo-1-fluoro-5-isothiocyanato-3-trifluoromethylbenzene

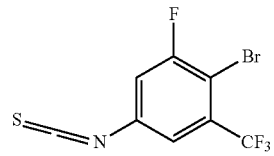

4-bromo-3-fluoro-5-trifluoromethylaniline (4.22 g, 16.4 mmol, Eq: 1.00) and calcium carbonate (3.44 g, 1.17 ml, 34.3 mmol, Eq: 2.1) were suspended in 50% aqueous dichloromethane (20 ml) mixture. The thick suspension was stirred vigorously at 0° C. Thiophosgene (2.07 g, 1.38 ml, 18.0 mmol, Eq: 1.1) was added slowly dropwise to the mixture. After the addition the mixture was stirred at 0° C. for 1.5 hr then stirred overnight at room temperature. The solids were filtered and the filtrate was extracted with dichloromethane. The combined organic phases were washed with water, brine, dried over sodium sulfate and concentrated in vacuo to afford 4.71 g (96%) of the desired material as a light brown solid.

$^1$H NMR (300 MHz, DMSO-$d_6$) δ ppm 7.84 (s, 1H) 7.96 (dd, J=9.06, 2.27 Hz, 1H)

(4-Bromo-3-fluoro-5-trifluoromethyl-phenylamino)-(methyl-$\lambda^4$sulfanylidene)-methyl-cyanamide

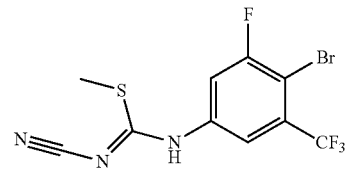 [SMILES: CS/C(=N\C#N)Nc1cc(F)c(Br)c(C(F)(F)F)c1]

2-bromo-1-fluoro-5-isothiocyanato-3-trifluoromethylbenzene (4.71 g, 15.7 mmol, Eq: 1.00) was dissolved in anhydrous methanol (30 ml). Sodium hydrogencyanamide (1.00 g, 15.7 mmol, Eq: 1) was added and the reaction was stirred for 1 hr at ambient temperature. Methyl iodide (4.46 g, 1.96 ml, 31.4 mmol, Eq: 2) was added dropwise and the reaction was stirred overnight at ambient temperature. The light brown suspension was filtered to afford 1.91 g (34%) of the desired product as a pink solid.

MS +m/z: 357.7. (M+1)

$^1$H NMR (300 MHz, DMSO-$d_6$) δ ppm 2.78 (s, 3H) 7.87 (s, 1H) 7.97 (dd, J=1.00 Hz, 1H) 10.38 (br. s, 1H)

Preparation of $N^5$-(4-bromo-3-fluoro-5-trifluoromethylphenyl)-1H-[1,2,4]-triazole-3,5-diamine (Intermediate 1)

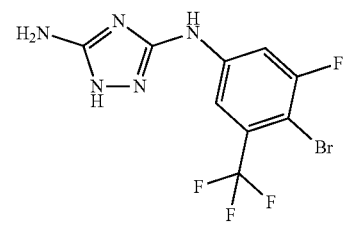

Hydrazine (1.71 g, 53.4 mmol, Eq: 10) was added to a stirred suspension of (4-Bromo-3-fluoro-5-trifluoromethyl-phenylamino)-(methyl-$\lambda^4$sulfanylidene)-methyl-cyanamide (1.9 g, 5.34 mmol, Eq: 1.00) in ethanol (30 ml). The mixture was heated to 70° C. for 1 hr. The reaction mixture was concentrated to a reduced volume (~5 ml) and water (~10 ml) was added dropwise while stirring. The suspension was stirred for 30 min. The precipitate was filtered and washed with water (~50 ml), then dried under high vacuum at 70° C. for two hours to filtered to afford 1.73 g (95%) of the desired product as a light pink solid.

MS +m/z: 339.9. (M+1)

$^1$H NMR (400 MHz, DMSO-$d_6$) δ ppm 6.03 (s, 2H) 7.81 (s, 1H) 7.86 (d, J=12.13 Hz, 1H) 9.52 (s, 1H) 11.40 (s, 1H)

Example 1

N$^5$-(3-Fluoro-4-phenylsulfanyl-5-trifluoromethyl-phenyl)-1H-[1,2,4]-triazole-3,5-diamine (Compound 1)

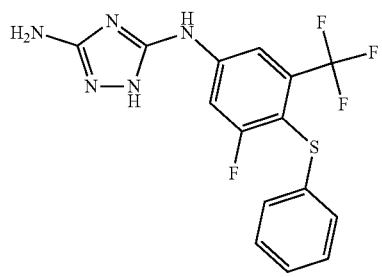 [SMILES: Nc1n[nH]c(Nc2cc(F)c(Sc3ccccc3)c(C(F)(F)F)c2)n1]

N$^5$-(4-Bromo-3-fluoro-5-trifluoromethylphenyl)-1H-[1,2,4]-triazole-3,5-diamine (intermediate 1) (66 mg, 194 μmol, Eq: 1.00), 1,1'-bis(diisopropylphosphino)ferrocene (12.2 mg, 29.1 Eq: 0.15) and sodium tert-butoxide (24.2 mg, 252 μmol, Eq: 1.3) were suspended in dioxane (1.25 ml). Pd(OAc)$_2$ (6.54 mg, 29.1 Eq: 0.15) and benzenethiol (22.5 mg, 20.8 μl, 204 μmol, Eq: 1.05) were added under an argon atmosphere. The reaction mixture was heated to 130° C. for 2 hours in the microwave. 1,1'-bis(diisopropylphosphino) ferrocene (24.4 mg, 58.2 μmol, Eq: 0.30) and Pd(OAc)$_2$ (13 mg, 58.2 μmol, Eq: 0.30) was added and the reaction mixture was heated to 130° C. for 1 hour. The reaction mixture was diluted with water and dichloromethane. The aqueous phase was extracted with dichloromethane and the combined organic phases were washed with brine, dried over Na$_2$SO$_4$ and stripped in vacua. The crude material was purified by silica gel chromatography (0-10% methanol in dichloromethane) to give a brown solid. The product was repurified by preparative HPLC (20% ACN: 0.3% TFA in water to 100% ACN) to afford 4 mg (4%) of the desired product as a white solid.

MS +m/z: 369.9. (M+1)

$^1$H NMR (400 MHz, MeOD) δ ppm 7.09-7.30 (m, 5H) 7.70-7.79 (in, 2H)

N*3*-(3-Chloro-4-phenylamino-phenyl)-1H-[1,2,4] triazole-3,5-diamine (Compound 2)

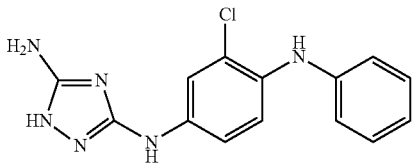

2-chloro-4-nitro-N-phenylaniline

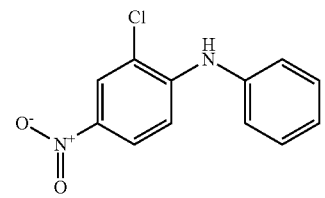 [SMILES: O=[N+]([O-])c1ccc(Nc2ccccc2)c(Cl)c1]

Charged sodium hydride (688.6 mg, 17.2 mmol, Eq: 1.48) into a 250-mL round-bottomed flask while purging with argon. Added N,N'-dimethylformamide (60 mL) and cooled the mixture in an ice bath. Added aniline (1.02 g, 1.00 mL, 11.0 mmol, Eq: 0.944) and stirred in ice bath for ~10 min; then charged 2-chloro-1-fluoro-4-nitrobenzene (2.04 g, 11.6 mmol, Eq: 1.00) into the cold reaction mixture in one portion. Monitored the reaction by HPLC: Stirred at 0° C. for 1 h, stirred at room temperature 17 h, then heated the reaction at 65° C. overnight. Cooled reaction mixture in an ice bath. Using 1 N hydrochloric acid solution the reaction was slowly quenched. Diluted the reaction mixture with water and extracted with ethyl acetate (3×). Combined organic layers and washed with water and saturated sodium chloride. Dried over magnesium sulfate, filtered, and concentrated. Obtained 2.94 g of crude material. Redissolved in dichloromethane and concentrated onto silica. Purified using a 220 g silica gel column on an Intelliflash 280; collected 28 mL fractions at 88 mL/min; equilibrated with hexanes; dry loaded; eluted 3 min with hexanes; increased from 0-50% dichloromethane/hexanes over 45 min; held at 50% dichloromethane/hexanes for 9 min. Obtained 700 mg (20.3%) of impure 2-chloro-4-nitro-N-phenylaniline (84% purity) as a yellow solid.

2-chloro-N1-phenylbenzene-1,4-diamine

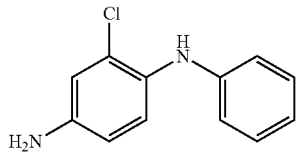 [SMILES: Nc1ccc(Nc2ccccc2)c(Cl)c1]

To the 250-mL round-bottomed flask containing 2-chloro-4-nitro-N-phenylaniline (700 mg, 2.82 mmol, Eq: 1.00) was added methanol (10 mL) and water (5 mL) followed by iron (786 mg, 14.1 mmol, Eq: 5.0) and ammonium chloride (1.51 g, 28.2 mmol, Eq: 10.0) all while purging with argon. Heat the mixture at reflux for 8 h. Filtered the reaction mixture through Celite, rinsing with methanol. Concentrated the filtrate, then dissolved the residue in ethyl acetate and added water. Added solid sodium bicarbonate until neutral. Split layers and washed the organics with water and saturated sodium chloride solution. Dried over sodium sulfate, filtered, and concentrated. Obtained 630 mg (82% yield at 80% purity) crude 2-chloro-N1-phenylbenzene-1,4-diamine as a brown oil. Used as is.

2-chloro-4-isothiocyanato-N-phenylaniline

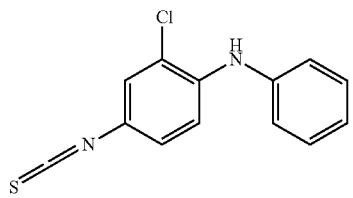

Purged the 50-mL round-bottomed flask containing 2-chloro-N1-phenylbenzene-1,4-diamine (630 mg, 2.88 mmol, Eq: 1.00) with argon. Added dichloromethane (30 mL) and cooled the mixture to 0° C. in an ice bath. Added 1,1'-thiocarbonyldiimidazole (770 mg, 4.32 mmol, Eq: 1.5) in one portion then removed the ice bath an allowed the reaction mixture to warm to room temperature. Stirred for 1 h. The reaction mixture was diluted with dichloromethane and concentrated onto silica. Purified using a 120 g silica gel column on an Intelliflash 280; collected peaks only in 28 mL fractions at 53 mL/min; equilibrated with hexanes; dry loaded; eluted for 3 min with hexanes; increased from 0-25% dichloromethane/hexanes over 15 min; held at 25% dichloromethane/hexanes for 2 min. Obtained 528.6 mg (59% yield at 84% purity) of 2-chloro-4-isothiocyanato-N-phenylaniline as a yellow solid.

(Z)-methyl N-3-chloro-4-(phenylamino)phenyl-N'-cyanocarbamidothioate

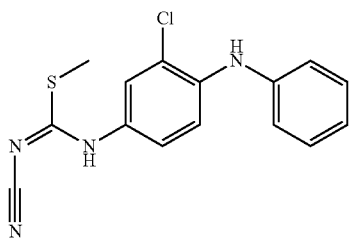 [SMILES: CS/C(=N/C#N)Nc1ccc(Nc2ccccc2)c(Cl)c1]

Charged cyanamide (101 mg, 2.4 mmol, Eq: 1.51) into a 50-mL round-bottomed flask while purging with argon. Added 0.5 M sodium methoxide in methanol (5.0 mL, 2.5 mmol, Eq: 1.57) at room temperature, then stirred for 15 min. Meanwhile, purged the 100-mL round-bottomed flask containing 2-chloro-4-isothiocyanato-N-phenylaniline (520 mg, 1.6 mmol, Eq: 1.00) with argon and added methanol (10 mL) and began stirring. Transferred the cyanamide mixture to the starting material mixture via syringe at room temperature. The solids dissolved after a short time of stirring. Stirred for a total of 1 h, then added iodomethane (431 mg, 0.19 mL, 3.04 mmol, Eq: 1.9) and stirred overnight at room temperature. Monitored the reaction by HPLC. Diluted the reaction mixture with dichloromethane and methanol, then concentrated onto silica gel. Purified using an 80 g silica gel column on an Intelliflash 280; collected peaks only in 28 mL fractions at 55 mL/min; equilibrated with hexanes; dry loaded; eluted 2 min with hexanes; increased from 0-50% ethyl acetate/hexanes over 22 min; held at 50% ethyl acetate/hexanes for 15 min. Obtained 302 mg (57% yield at 95% purity) of (Z)-methyl N-3-chloro-4-(phenylamino)phenyl-N-cyanocarbamimidothioate as a light brown solid.

N*3*-(3-Chloro-4-phenylamino-phenyl)-1H-[1,2,4]triazole-3,5-diamine (Compound 2)

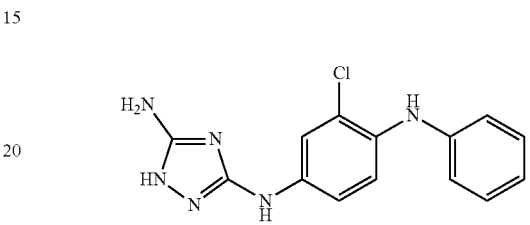

Purged the 2-neck, 100-mL round-bottomed flask, fitted with a vigroux column, containing the starting material, (Z)-methyl N-3-chloro-4-(phenylamino)phenyl-N-cyanocarbamimidothioate (302 mg, 953 µmol, Eq: 1.00), with argon. Added ethanol (15 mL) and hydrazine (306 mg, 0.30 mL, 9.56 mmol, Eq: 10.0). Heated at 65° C. for ~30 min, then removed an aliquot and took an HPLC: no starting material remained. Cooled the reaction and removed the solvent in vacuo. Obtained an oil that was subsequently redissolved in dichloromethane/methanol (1:1) and concentrated onto silica gel. Pre-purified using a 40 g silica gel column (0-10% methanol/dichloromethane with 1% ammonium hydroxide). Purified by prep-HPLC. Obtained 205 mg (71.5%) of N*3*-(3-Chloro-4-phenylamino-phenyl)-1H-[1,2,4]triazole-3,5-diamine as a light pink solid. MS calcd. for $C_{14}H_{13}ClN_6$ [(M+H)$^+$] 301.1, obsd. 300.8

N*3*-(3-Chloro-4-phenoxy-phenyl)-1H-[1,2,4]triazole-3,5-diamine (Compound 3)

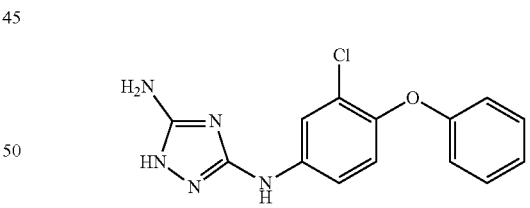

2-chloro-4-nitro-1-phenoxybenzene

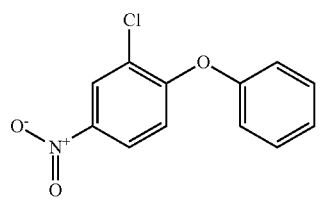 [SMILES: O=[N+]([O-])c1ccc(Oc2ccccc2)c(Cl)c1]

In a 250-mL round-bottomed flask, 2-chloro-1-fluoro-4-nitrobenzene (2.0 g, 11.4 mmol, Eq: 1.00), phenol (1.07 g, 11.4 mmol, Eq: 1.00) and potassium carbonate (3.15 g, 22.8 mmol, Eq: 2.0) were combined with N,N-dimethylformamide (22.8 mL). The reaction mixture was heated at 100° C. overnight. In the morning, the reaction mixture was poured over ice water, then the mixture was extracted with ethyl acetate. The organic phase was dried over sodium sulfate, filtered, then concentrated to afford 3.07 g (108%) of 2-chloro-4-nitro-1-phenoxybenzene as a tan oil. 1H NMR indicates the presence of some excess N,N-dimethylformamide.

3-chloro-4-phenoxyaniline

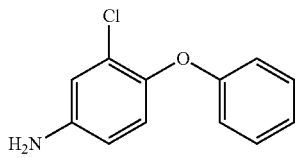

In a 250-mL round-bottomed flask, 2-chloro-4-nitro-1-phenoxybenzene (3.07 g, 12.3 mmol, Eq: 1.00), iron (3.43 g, 61.5 mmol, Eq: 5.0) and ammonium chloride (6.58 g, 123 mmol, Eq: 10) were combined with methanol (32.8 ml) to give a light brown suspension. Iron stuck to the magnetic stir bar. Water (16.4 mL) was added, then the reaction mixture became a milky-white suspension. The reaction mixture was refluxed for 6 h. After only 20 minutes, the reaction mixture was rust-colored. After 6 h at reflux, reverse phase HPLC shows complete conversion of the starting material to a more polar product. The reaction mixture was filtered, then concentrated to remove most of the methanol. The resulting crude suspension was extracted with ethyl acetate. The organic phase was dried (magnesium sulfate), filtered, then concentrated to give 2.5 g (92.5%) of 3-chloro-4-phenoxyaniline as a slightly tan oil.

2-chloro-4-isothiocyanato-1-phenoxybenzene

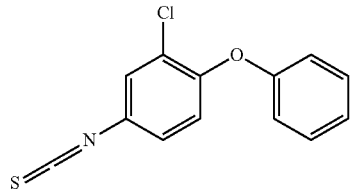

Purged the 1-L round-bottomed flask containing 3-chloro-4-phenoxyaniline (2.5 g, 11.4 mmol, Eq: 1.00) with argon. Added dichloromethane (120 mL) and cooled the mixture to 0° C. in an ice bath. Added 1,1'-thiocarbonyldiimidazole (2.43 g, 13.7 mmol, Eq: 1.2) in one portion then removed the ice bath and allowed the reaction mixture to warm to room temperature. After one hour the reaction was complete according to HPLC. The reaction mixture was diluted with dichloromethane and concentrated onto silica. Purified using a 330 g silica gel column on an Intelliflash 280; collected peaks only in 28 mL fractions at 86 mL/min; equilibrated with hexanes; dry loaded; eluted for 5 min with hexanes; increased from 0-25% dichloromethan/hexanes over 30 min. Obtained 1.69 g (56.7%) of 2-chloro-4-isothiocyanato-1-phenoxybenzene as a clear, colorless oil.

(Z)-methyl N-3-chloro-4-phenoxyphenyl-N'-cyanocarbamimidothioate

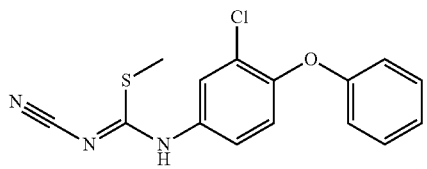 [SMILES: CS/C(=N\C#N)Nc1ccc(Oc2ccccc2)c(Cl)c1]

Charged cyanamide (350.6 mg, 8.34 mmol, Eq: 1.29) into a 50-mL round-bottomed flask while purging with argon. Added 0.5 M sodium methoxide in methanol (15.5 mL, 7.75 mmol, Eq: 1.2) at room temperature, then stirred for 15 min. Meanwhile, purged the 100-mL round-bottomed flask containing 2-chloro-4-isothiocyanato-1-phenoxybenzene (1.69 g, 6.46 mmol, Eq: 1.00) with argon and added methanol (25 mL) and began stirring. Transferred the cyanamide mixture to the starting material mixture via syringe at room temperature. The mixture became homogeneous after a short time of stirring. Stirred for a total of 1 h, then added iodomethane (1.38 g, 0.606 mL, 9.69 mmol, Eq: 1.5) and stirred overnight at room temperature. After 21 h, reaction was complete according to HPLC. Diluted with dichloromethane and methanol and concentrated onto silica gel. Purified using 120 g silica gel column on an Intelliflash 280; collected peaks only in 28 mL fractions at 80 mL/min; equilibrated with hexanes; dry loaded; eluted for 2.5 min with hexanes; increased from 0-50% ethyl acetate/hexanes over 27.5 min; held at 50% for 10 min. Obtained 1.34 g (65% yield) of (Z)-methyl N-3-chloro-4-phenoxyphenyl-N'-cyanocarbamimidothioate as a light yellow solid.

N*3*-(3-Chloro-4-phenoxy-phenyl)-1H-[1,2,4]triazole-3,5-diamine (Compound 3)

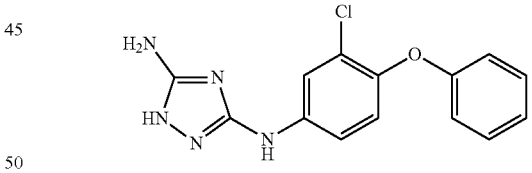

Purged the 3-neck, 250-mL round-bottomed flask, fitted with a vigroux column, containing (Z)-methyl N-3-chloro-4-phenoxyphenyl-N'-cyanocarbamimidothioate (1.33 g, 4.19 mmol, Eq: 1.00), with argon. Added ethanol (50 mL) and hydrazine (1.34 g, 1.31 mL, 41.9 mmol, Eq: 10.0). Heated at 65° C. for ~30 min, then removed an aliquot and took an HPLC: No starting material remained. Cooled the reaction and removed the solvent in vacuo. Obtained a foam that was subsequently redissolved in a dichloromethane/methanol (1:1) mixture and concentrated onto silica gel. Purified using an 80 g silica gel column on an Intelliflash 280; collected peaks only in 28 mL fractions at 53 mL/min; equilibrated with dichloromethane with 1% ammonium hydroxide; dry loaded; eluted 2 min with dichloromethane with 1% ammonium hydroxide; increased from 0-10% methanol/dichloromethane with 1% ammonium hydroxide;

held at 10% for 2 min. Obtained 1.1165 g (88.4%) of N*3*-(3-Chloro-4-phenoxy-phenyl)-1H-[1,2,4]triazole-3,5-diamine as a white solid. MS calcd. for $C_{14}H_{12}ClN_5O$ [(M+H)$^+$] 302.1, obsd. 302.3

N*3*-(3,5-Dichloro-4-phenylsulfanyl-phenyl)-1H-[1,2,4]triazole-3,5-diamine (Compound 4)

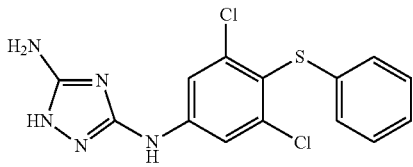 [SMILES: Nc1nc(Nc2cc(Cl)c(Sc3ccccc3)c(Cl)c2)n[nH]1]

(2,6-dichloro-4-nitrophenyl)(phenyl)sulfane

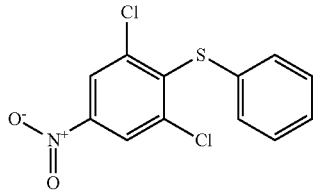 [SMILES: O=[N+]([O-])c1cc(Cl)c(Sc2ccccc2)c(Cl)c1]

In a 500-mL round-bottomed flask, 1,3-dichloro-2-fluoro-5-nitrobenzene (4.0 g, 19.0 mmol, Eq: 1.00), potassium carbonate (6.6 g, 47.8 mmol, Eq: 2.51) and benzenethiol (2.9 g, 2.7 ml, 26.3 mmol, Eq: 1.38) were combined with N,N-dimethylformamide (40 ml) to give a white suspension. This mixture was stirred at 100° C. for 8 hours. After this time, reverse-phase HPLC indicated complete conversion of the starting material to a single new product. The reaction mixture was combined with ice water, giving a yellow suspension. This suspension was extracted with ethyl acetate. The organic phase was dried over sodium sulfate, filtered, and concentrated to afford a brown oil. 1H NMR of the crude product was consistent with a new product, but excess N,N-dimethylformamide and thiophenol also appeared to be present. The crude product was loaded directly onto a 210 g Analogix column. Flash chromatography (using 100% hexanes) provided the purified product. Obtained 5.53 g (96.7%) of (2,6-dichloro-4-nitrophenyl)(phenyl)sulfane as an oily yellow solid.

3,5-dichloro-4-(phenylthio)aniline

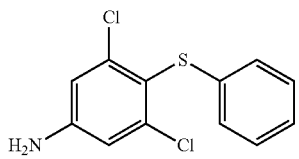

To the 250-mL round-bottomed flask containing (2,6-dichloro-4-nitrophenyl)(phenyl)sulfane (2.09 g, 6.96 mmol, Eq: 1.00), charged iron (1.94 g, 34.8 mmol, Eq: 5.0), ammonium chloride (3.72 g, 69.6 mmol, Eq: 10.0), methanol (42 mL), and water (21 mL). Heated to reflux. After 1.5 h, removed an aliquot and took an HPLC: the starting material had been consumed. Cooled reaction mixture and filtered it through a bed of Celite, rinsing with a large amount of methanol. Concentrated filtrate, then added ethyl acetate and stirred for an hour. Filtered off the solids and concentrated the filtrate. Obtained 1.846 g (82% yield at 84% purity) of 3,5-dichloro-4-(phenylthio)aniline as a light brown solid.

1,3-dichloro-5-isothiocyanate-2-phenylsulfinylbenzene

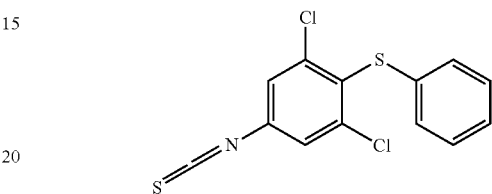

To the 250-mL round-bottomed flask containing 3,5-dichloro-4-(phenylthio)aniline (1.846 g, 6.83 mmol, Eq: 1.00), charged 1,1'-thiocarbonyldiimidazole (1.58 g, 8.88 mmol, Eq: 1.3) and dichloromethane (40 mL). Stirred overnight at room temperature. Diluted with dichloromethane and concentrated onto Celite. Purified using an 80 g silica gel column on an Intelliflash 280; collected peaks only in 28 mL fractions at 36 mL/min; equilibrated with hexanes; dry loaded on Celite; eluted 3 min with hexanes; increased from 0-10% dichloromethane/hexanes over 30 min. Obtained 1.64 g (77%) of 1,3-dichloro-5-isothiocyanato-2-phenylsulfinylbenzene as an orange solid.

(Z)-methyl N'-cyano-N-(3,5-dichloro-4-(phenylthio)phenyl)carbamimidothioate

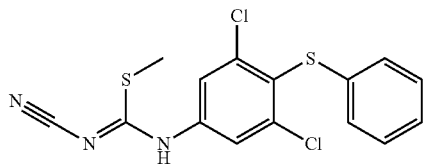 [SMILES: CS/C(=N\C#N)Nc1cc(Cl)c(Sc2ccccc2)c(Cl)c1]

Charged cyanamide (676 mg, 16.1 mmol, Eq: 3.08) into a 50-mL round-bottomed flask while purging with argon. Added 0.5 M sodium methoxide in methanol (16 mL, 8.00 mmol, Eq: 1.53) at room temperature. Meanwhile, added methanol (30 mL) and toluene (10 nap to the 250-mL round-bottomed flask containing 1,3-dichloro-5-isothiocyanato-2-phenylsulfinylbenzene (1.63 g, 5.22 mmol, Eq: 1.00). After 25 min of stirring the cyanamide mixture, transferred the cyanamide mixture to the isothiocyanate mixture using a syringe. Stirred at room temperature for 1 h, then removed an aliquot: HPLC showed no starting material remaining. Added iodomethane (1.14 g, 0.5 mL, 8.00 mmol, Eq: 1.53) to the reaction mixture and stirred overnight at room temperature. LC/MS after 16 h showed reaction was complete. Diluted the reaction mixture and concentrated onto Celite. Purified using a 150 g silica gel column on an Intelliflash 280; collected peaks only in 28 mL fractions at 76 mL/min; equilibrated with 10% ethyl acetate/hexanes; dry loaded; eluted 3 min with 10% ethyl acetate/hexanes; increased from 10-50% ethyl acetate/hexanes over 36 min; held at 50% for 10 min. Obtained 1.646 g (75% yield at 88% purity) of (Z)-methyl N'-cyano-N-(3,5-dichloro-4-(phenylthio)phenyl)carbamimidothioate as a white solid.

N*3*-(3,5-Dichloro-4-phenylsulfanyl-phenyl)-1H-[1,2,4]triazole-3,5-diamine (Compound 4)

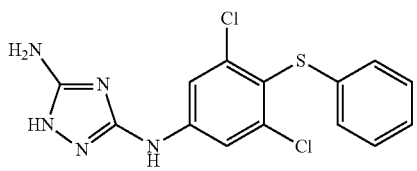 [SMILES: Nc1nc(Nc2cc(Cl)c(Sc3ccccc3)c(Cl)c2)n[nH]1]

Added ethanol (40 mL) and hydrazine (1.43 g, 1.4 mL, 44.6 mmol, Eq: 10.0) to the 100-mL round-bottomed flask containing (Z)-methyl N'-cyano-N-(3,5-dichloro-4-(phenylthio)phenyl)carbamimidothioate (1.64 g, 4.45 mmol, Eq: 1.00). Heated at reflux for 4 h; HPLC showed no starting material remaining. Cooled to room temperature. Concentrated onto Celite. Partially purified using a 120 g silica gel column on an Intelliflash 280; collected peaks only in 28 mL fractions at 76 mL/min; equilibrated using 5% methanol/dichloromethane with 1% ammonium hydroxide; dry loaded; eluted 4 min with 5% methanol/dichloromethane with 1% ammonium hydroxide; increased from 5-10% methanol/dichloromethane with 1% ammonium hydroxide over 24 min. Obtained 1.33 g (76.3% yield at 90% purity) of impure product as a yellow foam. Removed 94 mg of material and purified by prep-HPLC. Obtained 35.8 mg (38% recovery) of N*3*-(3,5-Dichloro-4-phenylsulfanyl-phenyl)-1H-[1,2,4]triazole-3,5-diamine as an off-white solid. 1H NMR (DMSO-d6) Shift: 11.41 (br. s, 1H), 9.53 (br. s, 1H), 7.81 (s, 2H), 6.91-7.38 (m, 5H), 6.07 (br. s, 2H). MS calcd. for C14H11Cl2N5S [(M+H)+] 352.0, obsd. 351.8.

N*3*-(4-Benzenesulfinyl-3,5-dichloro-phenyl)-1H-[1,2,4]triazole-3,5-diamine (Compound 5)

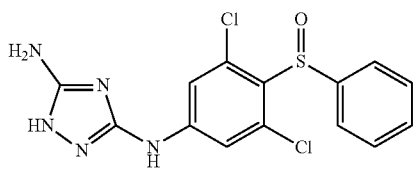 [SMILES: Nc1nc(Nc2cc(Cl)c(S(=O)c3ccccc3)c(Cl)c2)n[nH]1]

Charged N3-(3,5-dichloro-4-(phenylthio)phenyl)-1H-1,2,4-triazole-3,5-diamine (compound 4) (500 mg, 1.42 mmol, Eq: 1.00) into a 100-mL round-bottomed flask and added methanol (32 mL). To the mixture added a solution of oxone (2.62 g, 4.26 mmol, Eq: 3.0) in water (16 mL). Stirred at room temperature for 20 h. HPLC showed a mixture of sulfoxide and sulfone; all the starting material had been consumed. Stirred for another 24 h. The ratio of sulfoxide to sulfone, according to HPLC, was ~1:1. Added a second 50 mg scale reaction to the reaction mixture. Diluted the mixture with ethyl acetate and added water. Split the layers, but a gummy orange solid would not dissolve in either layer. Washed the organics with saturated sodium chloride, dried over sodium sulfate, filtered, and concentrated. Obtained an orange residue. Attempted to dissolve the residue in ethyl acetate and acetone, but methanol was needed to fully dissolve everything. Concentrated the mixture onto Celite. Purified using a 23 g spherical silica gel column on an Intelliflash 280; collected peaks only in 9 mL fractions at 32 mL/nin (~1 min/CV); equilibrated with 2% methanol/dichloromethane with 1% ammonium hydroxide; dry loaded; eluted 2 min with 2% methanol/dichloromethane with 1% ammonium hydroxide; increased from 2-8% methanol/dichloromethane with 1% ammonium hydroxide over 16 min; held at 8% for 7 min. Obtained 31.4 mg (5.7%) of N*3*-(4-Benzenesulfinyl-3,5-dichloro-phenyl)-1H-[1,2,4]triazole-3,5-diamine as an orange solid. MS calcd. for C14H11Cl2N5OS [(M+H)+] 368.0, obsd. 367.8.

N*3*-(4-Benzenesulfonyl-3,5-dichloro-phenyl-1H-[1,2,4]triazole-3,5-diamine (Compound 6)

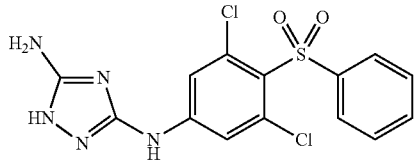 [SMILES: Nc1nc(Nc2cc(Cl)c(S(=O)(=O)c3ccccc3)c(Cl)c2)n[nH]1]

Charged N3-(3,5-dichloro-4-(phenylthio)phenyl)-1H-1,2,4-triazole-3,5-diamine (compound 4) (300 mg, 852 μmol, Eq: 1.00) into a 2-neck, 100-mL round-bottomed flask. Added methanol (24 mL) and began stirring. Meanwhile, dissolve the oxone (2.62 g, 4.26 mmol, Eq: 5.0) in water (12 mL). Added the oxone solution to the starting material solution via syringe. Immediately white solids crashed out. Stirred at 45° C. overnight. Took HPLC after 21 h, no starting material remained and the sulfone peak was the major peak. Cooled to room temperature. Diluted the reaction mixture with a large amount of ethyl acetate and washed with water. Split layers and washed with saturated sodium chloride. Dried over sodium sulfate, filtered, and concentrated. Redissolved in a small amount of methanol and diluted with acetone, then concentrated onto Celite. Purified using a 50 g spherical silica gel column on an Intelilflash 280; collected peaks only in 9 mL fractions at 40 mL/min (~2 min/CV); equilibrated with 1% methanol/dichloromethane with 1% ammonium hydroxide; dry loaded; eluted 4 min with 1% methanol/dichloromethane with 1% ammonium hydroxide; increased from 1-5% methanol/dichloromethane with 1% ammonium hydroxide over 38 min; held at 5% methanol/dichloromethane with 1% ammonium hydroxide for 8 min, then increased to 6% methanol/dichloromethane with 1% ammonium hydroxide over 10 min; held at 6% methanol/dichloromethane with 1% ammonium hydroxide for 6 min. Obtained 66 mg (20%) of N*3*-(4-Benzenesulfonyl-3,5-dichloro-phenyl)-1H-[1,2,4]triazole-3,5-diamine as an orange solid. MS calcd. for C14H11Cl2N5O2S [(M+H)+] 384.0, obsd. 384.0.

N3-(3,5-dichloro-4-(4-(trifluoromethyl)phenylthio)
phenyl)-1H-1,2,4-triazole-3,5-diamine (Compound
7)

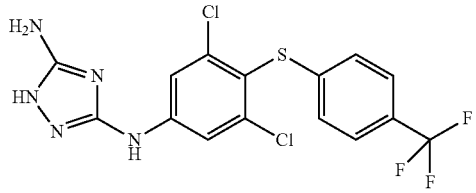 [SMILES: Nc1nc(Nc2cc(Cl)c(Sc3ccc(C(F)(F)F)cc3)c(Cl)c2)n[nH]1]

(2,6-dichloro-4-nitrophenyl)(4-(trifluoromethyl)phenyl)sulfane

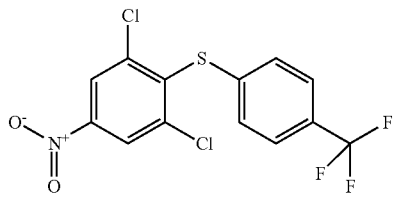 [SMILES: O=[N+]([O-])c1cc(Cl)c(Sc2ccc(C(F)(F)F)cc2)c(Cl)c1]

In a 250-mL round-bottomed flask, 4-(trifluoromethyl) benzenethiol (1 g, 5.61 mmol, Eq: 1.00), 1,3-dichloro-2-fluoro-5-nitrobenzene (1.18 g, 5.61 mmol, Eq: 1.00) and potassium carbonate (900 mg, 6.51 mmol, Eq: 1.16) were combined with N,N-dimethylformamide (22 mL) to give a yellow suspension. This mixture was heated at 100° C. overnight. In the morning, TLC indicated the presence of a new major product. TLC also showed complete consumption of the thiophenol and only a trace of the fluorobenzene remaining. The reaction mixture was poured over ice. The product only oiled out, giving a yellowish suspension. This suspension was extracted with ethyl acetate. The organic phase was dried over magnesium sulfate, filtered, then concentrated to a brown oil. This product was loaded directly on a 120 g SiliCycle column. Flash chromatography (5% ethyl acetate-hexanes ramped to 10 ethyl acetate-hexanes) afforded 1.13 g (47.7%) of (2,6-dichloro-4-nitrophenyl)(4-(trifluoromethyl)phenyl)sulfate at high purity as a yellow oil.

3,5-dichloro-4-(4-(trifluoromethyl)phenylthio)aniline

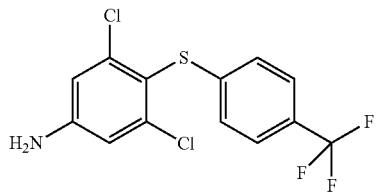 [SMILES: Nc1cc(Cl)c(Sc2ccc(C(F)(F)F)cc2)c(Cl)c1]

In a 250-mL round-bottomed flask, (2,6-dichloro-4-nitrophenyl)(4-(trifluoromethyl)phenyl)sulfane (1.13 g, 3.07 mmol, Eq: 1.00), iron (857 mg, 15.3 mmol, Eq: 5) and ammonium chloride (1.64 g, 30.7 mmol, Eq: 10) were combined with methanol (8 mL) to give a yellow suspension. Water (4.0 mL) was added. The reaction mixture was refluxed at 85° C. for 2 hours. After this time, TLC indicated complete conversion of the starting material to a dominant new product spot. The reaction mixture was cooled to room temperature, then it was partitioned between saturated aqueous sodium bicarbonate and ethyl acetate. The organic phase was dried over magnesium sulfate, filtered, then concentrated. Obtained 1.04 g (quantitative) of 3,5-dichloro-4-(4-(trifluoromethyl)-phenylthio)aniline as yellow crystals.

1,3-dichloro-5-isothiocyanato-2-(4-trifluoromethyl-phenylsulfanyl)benzene

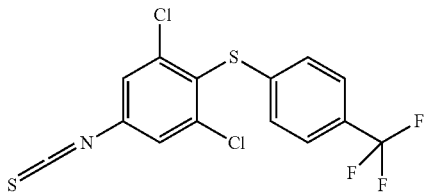

In a 1 L round-bottomed flask, 3,5-dichloro-4-(4-(trifluoromethyl)phenylthio)aniline (1.04 g, 3.08 mmol, Eq: 1.00) and 1,1'-thiocarbonyldiimidazole (600 mg, 3.37 mmol, Eq: 1.09) were combined with methylene chloride (22 mL) to give a light brown solution. The reaction mixture was stirred overnight at room temperature. After this time, TLC was consistent with new product formation (100% hexanes). The reaction mixture was concentrated over silica gel. Flash chromatography (100% hexanes) using an 80 gram Sili-Cycle column was used to purify the product. Obtained 462 mg (39.5%) of 1,3-dichloro-5-isothiocyanato-2-(4-trifluoromethylphenylsulfanyl)benzene as a yellow oil.

methyl N'-cyano-N-(3,5-dichloro-4-(4-(trifluoromethyl)phenylthio)phenyl)-carbamimidothioate

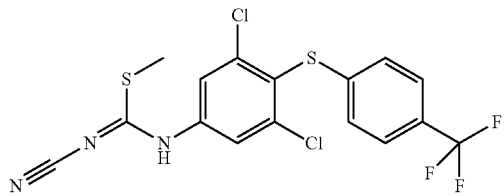 [SMILES: CSC(=NC#N)Nc1cc(Cl)c(Sc2ccc(C(F)(F)F)cc2)c(Cl)c1]

Charged cyanamide (112 mg, 2.67 mmol, Eq: 2.2) into a 5-mL round-bottomed flask while purging with argon. Added 0.5 M sodium methoxide in methanol (2.8 mL, 1.4 mmol, Eq: 1.15) and stirred at room temperature for 20 min. Meanwhile, purged the 100-mL round-bottomed flask containing 1,3-dichloro-5-isothiocyanato-2-(4-trifluoromethylphenylsulfanyl)benzene (462 mg, 1.22 mmol, Eq: 1.00) with argon, then added toluene (5 mL) and methanol (10 mL). The cyanamide mixture transferred to the isothiocyanate mixture via syringe. Stirred at room temperature for 75 min, then added iodomethane (345 mg, 152 μL, 2.43 mmol, Eq: 2.0). Stirred at room temperature overnight. In the morning, no solids had precipitated. TLC showed multiple spots. Concentrated onto Celite and purified using a 40 g silica gel column on an Intelliflash 280; collected peaks only in 9 mL fractions at 53 mL/min; equilibrated with hexanes; dry loaded; eluted 2 min with hexanes; increased from 0-50% ethyl acetate/hexanes over 28 min; held at 50% for 5 min. Obtained 509.5 mg (93%) of methyl N'-cyano-N-(3,5-dichloro-4-(4-(trifluoromethyl)phenylthio)phenyl)carbamimidothioate as a white solid.

N3-(3,5-dichloro-4-(4-(trifluoromethyl)phenylthio)phenyl)-1H-1,2,4-triazole-3,5-diamine (Compound 7)

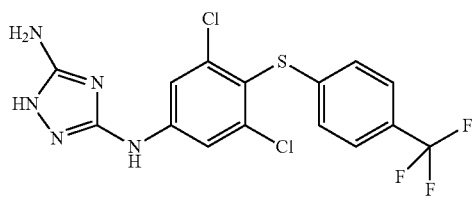 [SMILES: Nc1nc(Nc2cc(Cl)c(Sc3ccc(C(F)(F)F)cc3)c(Cl)c2)n[nH]1]

Added ethanol (25 mL) and hydrazine (204 mg, 200 µL, 6.37 mmol, Eq: 5.46) to the 250-mL round-bottomed flask containing methyl N'-cyano-N-(3,5-dichloro-4-(4-(trifluoromethyl)phenylthio)phenyl)carbamimidothioate (509.5 mg, 1.17 mmol, Eq: 1.00). Equipped the flask with a condenser and heated to reflux for 2 h. Cooled to room temperature; HPLC showed no starting material remained. Removed the solvent in vacuo. Obtained a white solid that turned reddish upon exposure to air. The material was analyzed on HPLC: a 10% impurity was present. Dissolved the crude product in methanol and concentrated onto Celite. Purified using a 24 g silica gel column on an Intelliflash 280; collected peaks only on 28 mL fractions at 32 mL/min; equilibrated with 2% methanol/dichloromethane with 1% ammonium hydroxide; dry loaded on Celite; eluted 2 min with 2% methanol/dichloromethane with 1% ammonium hydroxide; increased from 2-10% methanol/dichloromethane with 1% ammonium hydroxide over 13 min; held at 10% methanol/dichloromethane with 1% ammonium hydroxide for 6.25 min. Obtained 353 mg (72%) of N3-(3,5-dichloro-4-(4-(trifluoromethyl)phenylthio)phenyl)-1H-1,2,4-triazole-3,5-diamine as a white solid. MS calcd. for C15H10Cl2F3N5S [(M+H)+] 420.0, obsd. 419.8.

N3-(3,5-dichloro-4-(4-(trifluoromethyl)phenylsulfinyl)phenyl)-1H-1,2,4-triazole-3,5-diamine (Compound 8)

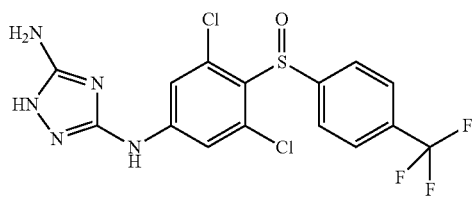 [SMILES: Nc1nc(Nc2cc(Cl)c(S(=O)c3ccc(C(F)(F)F)cc3)c(Cl)c2)n[nH]1]

Charged N3-(3,5-dichloro-4-(4-(trifluoromethyl)phenylthio)phenyl)-1H-1,2,4-triazole-3,5-diamine (compound 7) (127 mg, 302 µmol, Eq: 1.00) into a 25-mL round-bottomed flask and added methanol (5 mL) and oxone (187.2 mg, 305 µmol, Eq: 1.01). Monitored the reaction by HPLC: after 24 h, the reaction was mostly complete. Diluted the reaction mixture with water and filtered off the solids. Air dried for ~1 h, then attempted to dissolve the solids in ethyl acetate, but not all dissolved. Dissolved the remaining solids is methanol/dichloromethane mixture. Combined the ethyl acetate and methanol/dichloromethane mixtures together and concentrated onto Celite. Purified using a 23 g spherical silica gel column on an Intelliflash 280; collected peaks only in 9 mL fractions at 32 mL/min; equilibrated with 4% methanol/dichloromethane with 1% ammonium hydroxide; dry loaded; eluted 2 min with 4% methanol/dichloromethane with 1% ammonium hydroxide; increased from 4-10% methanol/dichloromethane with 1% ammonium hydroxide over 15 min; held at 10% methanol/dichloromethane with 1% ammonium hydroxide for 10 min. Obtained 76.8 mg (58%) of N3-(3,5-dichloro-4-(4-(trifluoromethyl)phenylsulfinyl)phenyl)-1H-1,2,4-triazole-3,5-diamine as a yellow solid. MS calcd. for C15H10Cl2F3N5OS [(M+H)+] 436.0, obsd. 435.8.

N*3*-[3,5-Dichloro-4-(4-trifluoromethyl-phenylsulfanyl)-phenyl]-1H-[1,2,4]triazole-3,5-diamine (Compound 9)

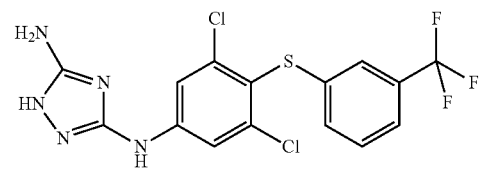 [SMILES: Nc1nc(Nc2cc(Cl)c(Sc3cccc(C(F)(F)F)c3)c(Cl)c2)n[nH]1]

(2,6-dichloro-4-nitrophenyl)(3-(trifluoromethyl)phenyl)sulfane

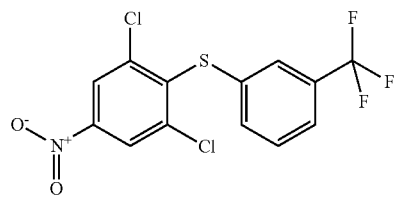 [SMILES: O=[N+]([O-])c1cc(Cl)c(Sc2cccc(C(F)(F)F)c2)c(Cl)c1]

In a 250-mL round-bottomed flask, 1,3-dichloro-2-fluoro-5-nitrobenzene (1.0 g, 4.76 mmol, Eq: 1.00), 3-trifluoromethyl thiophenol (848 mg, 4.76 mmol, Eq: 1.00) and potassium carbonate (658 mg, 4.76 mmol, Eq: 1.00) were combined with N,N-dimethylformamide to give a light brown suspension. The reaction mixture was heated at 100° C. for 3 hr. After this time, the reaction mixture was poured into ice to give a yellow suspension. The suspension was extracted with ethyl acetate. The organic phase was dried (sodium sulfate) filtered, then concentrated to give a brown oil. Purified by loading the crude directly onto a 120 g SiliCylcle column with a minimal amount of methylene chloride. Eluted using 100% hexanes ramped to 10% ethyl acetate hexanes. Obtained 1.62 g (92.4%) of impure product. The material was purified a second time using an 80 g column on an Intelliflash 280; collected peaks only in 28 mL fractions at 53 mL/min; equilibrated with hexanes; dry loaded; eluted 4 min with hexanes; increased from 0-50% dichloromethane/hexanes over 20 min. Obtained 730 mg (41.6%) of pure (2,6-dichloro-4-nitrophenyl)(3-(trifluoromethyl)phenyl)sulfane as a yellow oil.

3,5-dichloro-4-(3-(trifluoromethyl)phenylthio)aniline

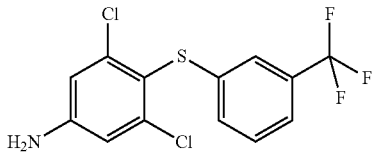 [SMILES: Nc1cc(Cl)c(Sc2cccc(C(F)(F)F)c2)c(Cl)c1]

Charged methanol (15 mL) to the 250-mL round-bottomed flask containing (2,6-dichloro-4-nitrophenyl)(3-(trifluoromethyl)phenyl)sulfane (730 mg, 1.98 mmol, Eq: 1.00). Added iron (565.6 mg, 10.1 mmol, Eq: 5.11) and ammonium chloride (1.06 g, 19.8 mmol, Eq: 10.0) in water (5 mL). Heated at reflux for ~1.5 h, then took an HPLC that showed the reaction was complete. Cooled the reaction mixture to room temperature, then filtered through a bed of Celite rinsing with methanol. Concentrated the filtrate and added ethyl acetate. Filtered off the solids and concentrated the filtrate. Obtained 578.8 mg (84%) of 3,5-dichloro-4-(3-(trifluoromethyl)phenylthio)aniline as a yellow solid.

1,3-dichloro-5-isothiocyanato-2-(3-trifluoromethyl-phenylsulfanyl)benzene

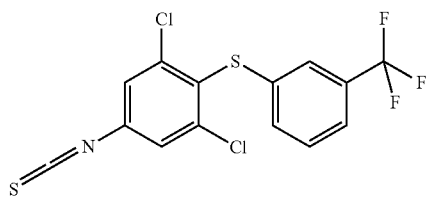

Added 1,1'-thiocarbonyldiimidazole (397 mg, 2.22 mmol, Eq: 1.3) and dichloromethane (20 mL) to the round-bottomed flask containing 3,5-dichloro-4-(3-(trifluoromethyl)phenylthio)aniline (578.8 mg, 1.71 mmol, Eq: 1.00) while purging with argon. Stirred over weekend. HPLC showed two major peaks, but no starting material. Diluted the reaction mixture with dichloromethane and concentrated onto Celite. Purified using a 40 g silica gel column on an Intelliflash 280; collected peaks only in 28 mL fractions at 53 mL/min; equilibrated with hexanes; dry loaded; eluted 2 min with hexanes; increased from 0-25% dichloromethane/hexanes over 13 min; held at 25% for 3 min. Obtained 267.5 mg (41%) of 1,3-dichloro-5-isothiocyanato-2-(3-trifluoromethylphenylsulfanyl)-benzene as an orange solid.

(Z)-methyl N'-cyano-N-(3,5-dichloro-4-(3-(trifluoromethyl)phenylthio)phenyl)-carbamimidothioate

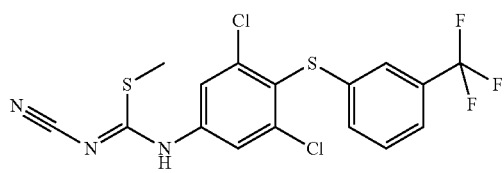 [SMILES: CS/C(=N\C#N)Nc1cc(Cl)c(Sc2cccc(C(F)(F)F)c2)c(Cl)c1]

Charged cyanamide (67.2 mg, 1.6 mmol, Eq: 2.34) into 10-mL round-bottomed flask while purging with argon. Added 0.5 M sodium methoxide in methanol (1.8 mL, 900 µmol, Eq: 1.32) and stirred at room temperature for 20 min. Meanwhile, dissolved 1,3-dichloro-5-isothiocyanato-2-(3-trifluoromethylphenylsulfanyl)benzene (260 mg, 684 µmol, Eq: 1.00) in toluene (2.5 mL), then added methanol (5 mL) all while purging with argon. After the 20 min, added the cyanamide mixture to the isothiocyanate mixture via syringe. Stirred at room temperature for 1.5 h, then added iodomethane (194 mg, 85.5 µL, 1.37 mmol, Eq: 2.0) and stirred overnight at room temperature. HPLC after 20 h, showed the reaction was complete. Diluted the mixture with methanol and ethyl acetate. Heated to a boil with a heat gun. Once all the solids were in solution stopped heating and added Celite. Concentrated the mixture. Purified using a 25 g SiliCycle HP silica gel column on an Intelliflash 280; collected peaks only in 28 mL fractions at 32 mL/min; equilibrated with 25% ethyl acetate/hexanes; dry loaded; eluted 2 min with 25% ethyl acetate/hexanes; increased from 25-60% ethyl acetate/hexanes over 15 min. Obtained 194 mg (64%) of (Z)-methyl N'-cyano-N-(3,5-dichloro-4-(3-(trifluoromethyl)phenylthio)phenyl)-carbamimidothioate as a white solid.

N*3*-[3,5-Dichloro-4-(4-trifluoromethyl-phenylsulfanyl)-phenyl]-1H-[1,2,4]triazole-3,5-diamine (Compound 9)

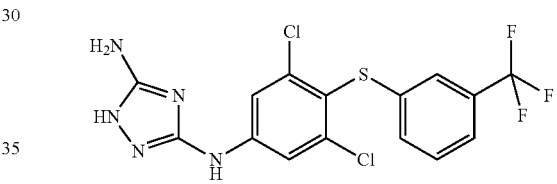

Added ethanol (20 mL) and hydrazine (71.2 mg, 69.8 µL, 2.22 mmol, Eq: 5.00) to the 250-mL round-bottomed flask contained the starting material, (Z)-methyl N'-cyano-N-(3, 5-dichloro-4-(3-(trifluoromethyl)phenylthio)phenyl)-carbamimidothioate (194 mg, 445 µmol, Eq: 1.00). Heated at reflux for 1.25 h, then the reaction was complete according to HPLC. Cooled the reaction mixture, then removed the solvent in vacuo. Placed in a 50° C. vacuum oven for 3 days. Obtained 175 mg (92%) of N*3*-[3,5-Dichloro-4-(4-trifluoromethyl-phenylsulfanyl)-phenyl]-1H-[1,2,4]triazole-3,5-diamine as an off-white solid. 1H NMR (DMSO-d6) Shift: 11.44 (br. s, 1H), 9.60 (br. s, 1H), 7.84 (s, 2H), 7.42-7.61 (m, 2H), 7.12-7.40 (m, 2H), 6.08 (s, 2H). MS calcd. for C15H10Cl2F3N5S [(M+H)+] 420.0, obsd. 419.8.

N*3*-[3,5-Dichloro-4-(2-trifluoromethyl-phenylsulfanyl)-phenyl]-1H-[1,2,4]triazole-3,5-diamine (Compound 10)

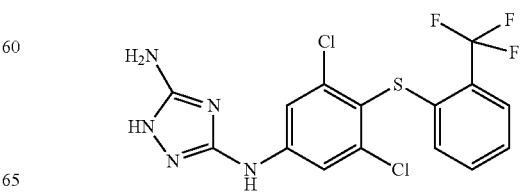

(2,6-dichloro-4-nitrophenyl)(2-(trifluoromethyl)phenyl)sulfane

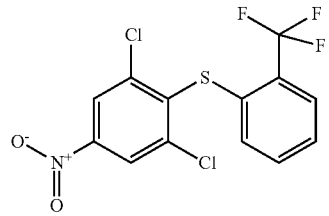 [SMILES: O=[N+]([O-])c1cc(Cl)c(Sc2ccccc2C(F)(F)F)c(Cl)c1]

In a 250-mL round-bottomed flask, 1,3-dichloro-2-fluoro-5-nitrobenzene (1.22 g, 5.81 mmol, Eq: 1.00), 2-(trifluoromethyl)benzenethiol (1.01 g, 5.67 mmol, Eq: 0.976) and potassium carbonate (0.98 g, 7.09 mmol, Eq: 1.22) were combined with N,N-dimethylformamide (22 mL) to give a light brown suspension. The reaction mixture was heated at 100° C. for 3.5 hrs. After this time, the reaction mixture was partitioned between ethyl acetate and water. The organic phase was dried over sodium sulfate, filtered, and concentrated to a brown oil. This crude product was dissolved in methylene chloride, then the mixture was concentrated over silica gel. The silica gel supported crude product was loaded onto a 120 gram silica gel column. Flash chromatography (100% hexanes ramped to 5% ethyl acetate in hexanes) provided 1.76 g (82.3%) of (2,6-dichloro-4-nitrophenyl)(2-(trifluoromethyl)phenyl)sulfane as a light yellow solid.

3,5-dichloro-4-(2-(trifluoromethyl)phenylthio)aniline

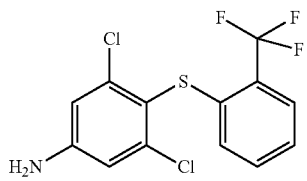 [SMILES: Nc1cc(Cl)c(Sc2ccccc2C(F)(F)F)c(Cl)c1]

Charged methanol (40 mL), iron (1.33 g, 23.8 mmol, Eq: 5.0), ammonium chloride (2.55 g, 47.7 mmol, Eq: 10), and water (20 mL) to the 250-mL round-bottomed flask containing (2,6-dichloro-4-nitrophenyl)(2-(trifluoromethyl)phenyl)sulfane (1.756 g, 4.77 mmol, Eq: 1.00). Stirred at reflux for 1.5 h: HPLC showed the reaction was complete. Cooled the reaction mixture then filtered through a bed of Celite, rinsing with methanol. Concentrated and added ethyl acetate. Filtered off the solids, rinsing with ethyl acetate, and concentrated the filtrate. Obtained 1.425 g (86%) of 3,5-dichloro-4-(2-(trifluoromethyl)phenylthio)aniline as a grey solid.

1,3-dichloro-5-isothiocyanato-2-(2-trifluoromethylphenylsulfanyl)benzene

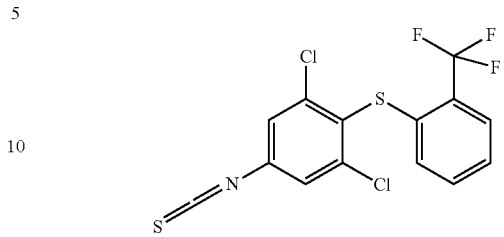

Charged 1,1'-thiocarbonyldiimidazole (1.0 g, 5.61 mmol, Eq: 1.33) and dichloromethane (30 mL) to the 250-mL round-bottomed flask containing 3,5-dichloro-4-(2-(trifluoromethyl)phenylthio)aniline (1.425 g, 4.21 mmol, Eq: 1.00), while purging with argon. Stirred at room temperature overnight. In morning, the HPLC showed no starting material. Diluted the mixture with dichloromethane and concentrated onto Celite. Purified using a 40 g silica gel column on an Intelliflash 280; collected peaks only in 28 mL fractions at 53 mL/min; equilibrated with hexanes; dry loaded; eluted 2 min with hexanes, then increased from 0-25% dichloromethane/hexanes over 15 min; held at 25% for 3 min. Obtained 980 mg (60%) of 1,3-dichloro-5-isothiocyanato-2-(2-trifluoromethylphenylsulfanyl)benzene as a yellow solid.

(Z)-methyl N'-cyano-N-(3,5-dichloro-4-(2-(trifluoromethyl)phenylthio)phenyl)carbamimidothioate

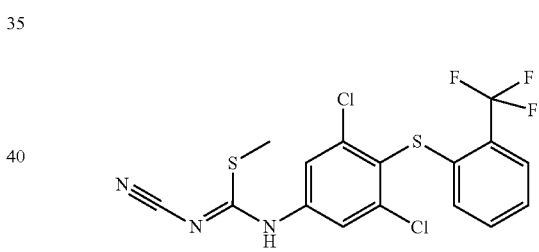

Charged cyanamide (220.4 mg, 5.24 mmol, Eq: 2.04) into a 25-mL round-bottomed flask while purging with argon. Added 0.5 M sodium methoxide in methanol (6.7 mL, 3.35 mmol, Eq: 1.31) and began stirring. Meanwhile, dissolved the isothiocyanate (975 mg, 2.56 mmol, Eq: 1.00) in toluene (5 mL) and added methanol (10 mL) all while purging with argon. After 10 min, the cyanamide mixture was added to the starting material mixture via syringe. Stirred at room temperature for 2 h, then added iodomethane (729 mg, 0.321 mL, 5.13 mmol, Eq: 2.00) and stirred for 4 days. Placed the reaction mixture in the freezer for 2 h, then filtered off the solids. The solids were air dried and the filtrate was concentrated onto Celite. The solid was 660 mg of product. The filtrate was purified using a 24 g silica gel column on an Intelliflash 280; collected peaks only in 28 mL fractions at 32 mL/min; equilibrated with 25% ethyl acetate/hexanes; dry loaded; eluted 2 min with 25% ethyl acetate/hexanes; increased from 25-60% ethyl acetate/hexanes over 15 min; held at 60% for 5 min. Obtained 202 mg of product. Obtained a total of 860 mg (76%) of (Z)-methyl N'-cyano-N-(3,5-dichloro-4-(2-(trifluoromethyl)phenylthio)phenyl)carbamimidothioate as a white solid.

N*3*-[3,5-Dichloro-4-(2-trifluoromethyl-phenylsulfanyl)-phenyl]-1H-[1,2,4]triazole-3,5-diamine (Compound 10)

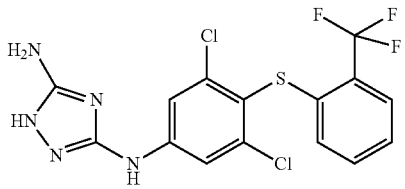 [SMILES: Nc1nc(Nc2cc(Cl)c(Sc3ccccc3C(F)(F)F)c(Cl)c2)n[nH]1]

Added ethanol (30 mL) and hydrazine (306 mg, 300 µL, 9.56 mmol, Eq: 4.91) to the 250-mL round-bottomed flask containing (Z)-methyl N'-cyano-N-(3,5-dichloro-4-(2-(trifluoromethyl)phenylthio)phenyl) carbamimidothioate (850 mg, 1.95 mmol, Eq: 1.00). Heated at reflux. After 1.5 h the reaction was complete according to HPLC. Cooled reaction and concentrated in vacuo. Placed in a 50° C. vacuum oven for 3 days. Obtained 860 mg of crude product. Dissolved the solids in methanol and concentrated onto Celite. Purified using a 40 g silica gel column on an Intelliflash 280; collected peaks only in 28 mL fractions at 53 mL/min (1 min/CV); equilibrated with 5% methanol/dichloromethane with 1% ammonium hydroxide; dry loaded; eluted 2 min with 5% methanol/dichloromethane with 1% ammonium hydroxide; increased from 5-10% methanol/dichloromethane with 1% ammonium hydroxide over 12 min. Obtained 647 mg (79%) of N*3*-[3,5-Dichloro-4-(2-trifluoromethyl-phenylsulfanyl)-phenyl]-1H-[1,2,4]triazole-3,5-diamine as an off-white solid. MS calcd. for C15H10Cl2F3N5S [(M+H)+] 420.0, obsd. 419.8.

N*3*-[3,5-Dichloro-4-(4-trifluoromethyl-benzenesulfinyl)-phenyl]-1H-[1,2,4]triazole-3,5-diamine (Compound 11)

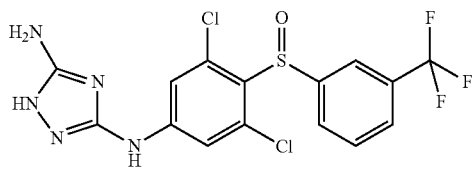 [SMILES: Nc1nc(Nc2cc(Cl)c(S(=O)c3cccc(C(F)(F)F)c3)c(Cl)c2)n[nH]1]

Added methanol (10 mL) and oxone (843 mg, 1.37 mmol, Eq: 4.0) to the 250-mL round-bottomed flask containing N3-(3,5-dichloro-4-(3-(trifluoromethyl)phenylthio)phenyl)-1H-1,2,4-triazole-3,5-diamine (compound 9) (144 mg, 343 µmol, Eq: 1.00). Heated the reaction at 60° C. overnight. HPLC and LC/MS showed that only sulfoxide was present. Cooled the mixture to room temperature. Diluted with water and extracted with ethyl acetate. Split layers and washed the organics with saturated sodium chloride. Dried organics over sodium sulfate, filtered, and concentrated onto Celite. Purified using a 24 g silica gel column on an Intelliflash 280; collected peaks only in 9 mL fractions at 32 mL/min (1 min/CV); equilibrated with 5% methanol/dichloromethane with 1% ammonium hydroxide; dry loaded; eluted 2 min with 5% methanol/dichloromethane with 1% ammonium hydroxide; increased from 5-10% methanol/dichloromethane with 1% ammonium hydroxide over 12 min; held at 10% methanol/dichloromethane with 1% ammonium hydroxide for 2 min. Obtained 42 mg (26%) of N*3*-[3,5-Dichloro-4-(4-trifluoromethyl-benzenesulfinyl)-phenyl]-1H-[1,2,4]triazole-3,5-diamine as a yellow solid. MS calcd. for C15H10Cl2F3N5OS [(M+H)+] 436.0, obsd. 435.8.

4-[4-(5-Amino-1H-[1,2,4]triazol-3-ylamino)-2,6-dichloro-phenylsulfanyl]-benzonitrile (Compound 12)

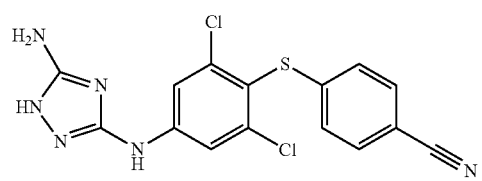 [SMILES: N#Cc1ccc(Sc2c(Cl)cc(Nc3n[nH]c(N)n3)cc2Cl)cc1]

4-(2,6-dichloro-4-nitrophenylthio)benzonitrile

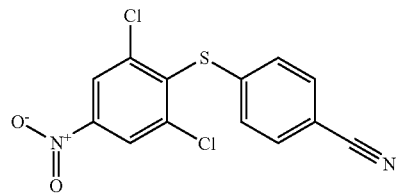 [SMILES: N#Cc1ccc(Sc2c(Cl)cc([N+](=O)[O-])cc2Cl)cc1]

In a 250-mL round-bottomed flask, 1,3-dichloro-2-fluoro-5-nitrobenzene (1.5 g, 7.14 mmol, Eq: 1.00), 4-mercaptobenzonitrile (966 mg, 7.14 mmol, Eq: 1.00) and potassium carbonate (1.09 g, 7.86 mmol, Eq: 1.1) were combined with N,N-dimethylformamide (30 mL) to give a light brown suspension. The reaction mixture was heated at 100° C. for 3.5 hrs. After this time the mixture was poured into water to give a yellow suspension. The suspension was extracted with ethyl acetate, and the organic phase was dried over sodium sulfate, filtered, and concentrated to afford the crude product as a yellow oil. This product was dissolved in methylene chloride and the resulting solution was concentrated over silica gel. The silica-gel supported crude product was loaded onto a 120 gram silica gel column. Flash chromatography (100% hexanes ramped to 5% ethyl acetate in hexanes) afforded 1.31 g (56.4%) of 4-(2,6-dichloro-4-nitrophenylthio)benzonitrile as a yellow solid.

4-(4-amino-2,6-dichlorophenylthio)benzonitrile

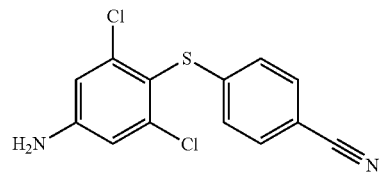 [SMILES: N#Cc1ccc(Sc2c(Cl)cc(N)cc2Cl)cc1]

Added ammonium chloride (2.37 g, 44.3 mmol, Eq: 10.0), iron (1.24 g, 22.1 mmol, Eq: 5.0), methanol (30 mL), and water (10 mL) to the 250-mL round-bottomed flask containing 4-(2,6-dichloro-4-nitrophenylthio)benzonitrile (1.44 g, 4.43 mmol, Eq: 1.00). Heated to reflux. After 1.25 h the reaction was complete according to HPLC. Cooled the reaction mixture to room temperature, then filtered the mixture through a bed of Celite, rinsing with copious amounts of methanol. Concentrated the filtrate, then added ethyl acetate and filtered off the solids. The filtrate was concentrated and dried over the weekend in a 50° C. vacuum oven. Obtained 567 mg (40%) of 4-(4-amino-2,6-dichlorophenylthio)benzonitrile as a yellow solid.

4-(2,6-Dichloro-4-isothiocyanatophenylsulfanyl) benzonitrile

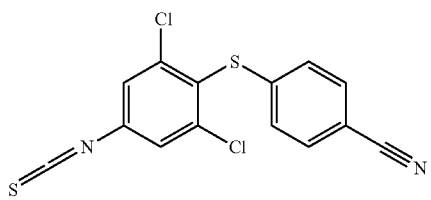

Added dichloromethane (10 mL) and 1,1'-thiocarbonyldiimidazole (440 mg, 2.47 mmol, Eq: 1.3) to the 250-mL round-bottomed flask containing 4-(4-amino-2,6-dichlorophenylthio)benzonitrile (560 mg, 1.9 mmol, Eq: 1.00). Stirred at room temperature overnight. TLC in 1:3 ethyl acetate/hexanes showed starting material remaining. Added more 1,1'-thiocarbonyldiimidazole (440 mg, 2.47 mmol, Eq: 1.3) and stirred overnight. TLC again showed a large starting material spot, but HPLC and LC/MS showed that it was not starting material. Concentrated the reaction mixture onto Celite. Purified using a 24 g silica gel column on an Intelliflash 280; collected peaks only in 28 mL fractions at 32 mL/min; equilibrated with hexanes; dry loaded; eluted 2 min with hexanes; increased from 0-15% dichloromethane/hexanes over 10 min, but no peaks eluted. Increased from 15-50% dichloromethane/hexanes over 20 min. Obtained 351 mg (52%) of 4-(2,6-Dichloro-4-isothiocyanatophenylsulfanyl)benzonitrile as a white solid.

(Z)-methyl N'-cyano-N-(3,5-dichloro-4-(4-cyanophenylthio)phenyl)-carbamimidothioate

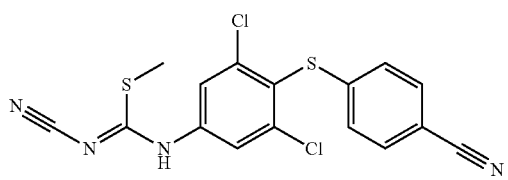 [SMILES: CS/C(=N\C#N)Nc1cc(Cl)c(Sc2ccc(C#N)cc2)c(Cl)c1]

While purging with argon, charged cyanamide (147 mg, 3.5 mmol, Eq: 3.42) into a 10 mL round-bottomed flask, then added 0.5 M sodium methoxide in methanol (2.66 mL, 1.33 mmol, Eq: 1.3). Stirred at room temperature for ~15 min. Meanwhile, dissolved 4-(2,6-Dichloro-4-isothiocyanatophenylsulfanyl)benzonitrile (345 mg, 1.02 mmol, Eq: 1.00) in toluene (3 mL), then added methanol (7 mL). Added the cyanamide mixture to the isothiocyanate mixture via syringe. Stirred at room temperature for 1 h, then removed an aliquot for HPLC: very little starting material remained. Added iodomethane (295 mg, 0.130 mL, 2.08 mmol, Eq: 2.03) at this time. Stirred over weekend. A white precipitate formed. Placed the reaction mixture in the freezer for 4 h. Filtered off the solids rinsing with cold methanol. Air dried and obtained 204 mg of a white solid, which was pure product according to $^1$H NMR, LC/MS, and HPLC. Also, concentrated the filtrate onto Celite and purified using a 40 g silica gel column on an Intelliflash 280; collected peaks only in 9 mL fractions at 53 mL/min; equilibrated with 20% ethyl acetate/hexanes; dry loaded; eluted 2 min with 20% ethyl acetate/hexanes; increased from 20-50% ethyl acetate/hexanes over 15 min; held at 50% ethyl acetate/hexanes for 3 min. Obtained 40 mg of product. Obtained a total of 240 mg (59% yield) of (Z)-methyl N'-cyano-N-(3,5-dichloro-4-(4-cyanophenylthio)phenyl)carbamimidothioate as a white solid.

4-[4-(5-Amino-1H-[1,2,4]triazol-3-ylamino)-2,6-dichloro-phenylsulfanyl]-benzonitrile (Compound 12)

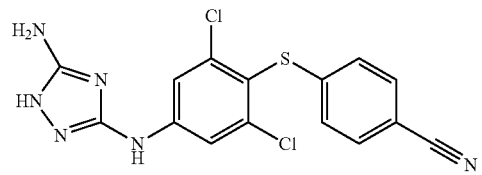 [SMILES: N#Cc1ccc(Sc2c(Cl)cc(Nc3n[nH]c(N)n3)cc2Cl)cc1]

Added ethanol (10 mL) and hydrazine (117 mg, 115 µL, 3.66 mmol, Eq: 6.0) to the round-bottomed flask containing (Z)-methyl N'-cyano-N-(3,5-dichloro-4-(4-cyanophenylthio)phenyl)carbamimidothioate (240 mg, 610 µmol, Eq: 1.00). Heated at reflux for 1 h. Observed that a larger amount of solids was present in the reaction mixture. Removed an aliquot and tried to dissolve the solid in acetonitrile/methanol mixture with heat, but not all would dissolve. Cooled the mixture to room temperature. Placed the reaction mixture in the freezer for 2 h. Filtered off the solid rinsing with cold ethanol. Air dried overnight. Obtained 196 mg (85%) of 4-[4-(5-Amino-1H-[1,2,4]triazol-3-ylamino)-2,6-dichloro-phenylsulfanyl]-benzonitrile as a white solid. MS calcd. for C15H10Cl2N6S [(M+H)+] 377.0, obsd. 376.8.

4-[4-(5-Amino-1H-[1,2,4]triazol-3-ylamino)-2,6-dichloro-benzenesulfinyl]-benzonitrile (Compound 13)

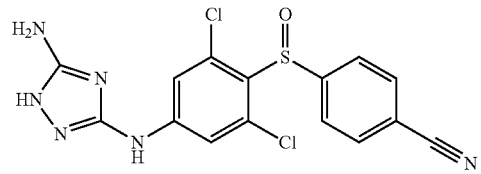 [SMILES: N#Cc1ccc(S(=O)c2c(Cl)cc(Nc3n[nH]c(N)n3)cc2Cl)cc1]

Charged 4-(4-(5-amino-1H-1,2,4-triazol-3-ylamino)-2,6-dichlorophenylthio)benzonitrile (compound 12) (160 mg, 424 µmol, Eq: 1.00; Joe Intermediate G) into a 5-mL round-bottomed flask, then added methanol (10 mL) and oxone (1.3 g, 2.12 mmol, Eq: 5.0). Heated at reflux over for 3 days. Cooled to room temperature and took HPLC, no starting material remained. Filtered rinsing with methanol and concentrated the filtrate onto Celite. Purified using a 25 g small particle size, silica gel column on an Intelliflash 280;

collected peaks only in 9 mL fractions at 33 mL/min (~1 min/CV); equilibrated with 5% methanol/dichloromethane with 1% ammonium hydroxide; dry loaded; eluted 2 min with 5% methanol/dichloromethane with 1% ammonium hydroxide; increased from 5-10% methanol/dichloromethane with 1% ammonium hydroxide over 18 min; held at 10% methanol/dichloromethane with 1% ammonium hydroxide for 4 min. Obtained 5.5 mg (3%) of 4-[4-(5-Amino-1H-[1,2,4]triazol-3-ylamino)-2,6-dichloro-benzenesulfinyl]-benzonitrile as a brown solid. MS calcd. for C15H10Cl2N6OS [(M+H)+] 393.0, obsd. 392.8.

4-[4-(5-Amino-1H-[1,2,4]triazol-3-ylamino)-2,6-dichloro-benzenesulfinyl]-benzonitrile (Compound 14)

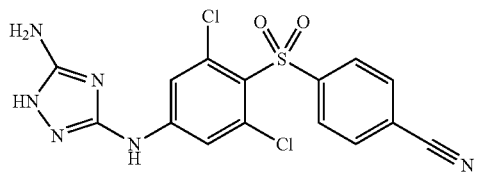

Charged 4-(4-(5-amino-1H-1,2,4-triazol-3-ylamino)-2,6-dichlorophenylthio)benzonitrile (compound 12) (160 mg, 424 μmol, Eq: 1.00) into a 5-mL round-bottomed flask, then added methanol (10 mL) and oxone (1.3 g, 2.12 mmol, Eq: 5.0). Heated at reflux over for 3 days. Cooled to room temperature and took HPLC, no starting material remained. Filtered rinsing with methanol and concentrated the filtrate onto Celite. Purified using a 25 g small particle size, silica gel column on an Intelliflash 280; collected peaks only in 9 mL fractions at 33 mL/min (~1 min/CV); equilibrated with 5% methanol/dichloromethane with 1% ammonium hydroxide; dry loaded; eluted 2 min with 5% methanol/dichloromethane with 1% ammonium hydroxide; increased from 5-10% methanol/dichloromethane with 1% ammonium hydroxide over 18 min; held at 10% methanol/dichloromethane with 1% ammonium hydroxide for 4 min. Obtained 17.2 mg (9.6%) of 4-[4-(5-Amino-1H-[1,2,4]triazol-3-ylamino)-2,6-dichloro-benzenesulfonyl]-benzonitrile as a brown solid. MS calcd. for C15H10Cl2N6O2S [(M+H)+] 409.0, obsd. 408.8.

4-[4-(5-Amino-1H-[1,2,4]triazol-3-ylamino)-2-chloro-6-trifluoromethyl-phenylsulfanyl]-benzoic acid methyl ester (Compound 15)

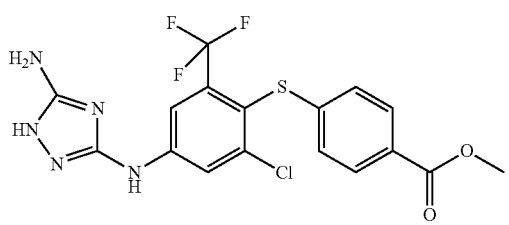 [SMILES: COC(=O)c1ccc(Sc2c(Cl)cc(Nc3n[nH]c(N)n3)cc2C(F)(F)F)cc1]

4-(2-chloro-4-nitro-6-(trifluoromethyl)phenylthio)benzoate

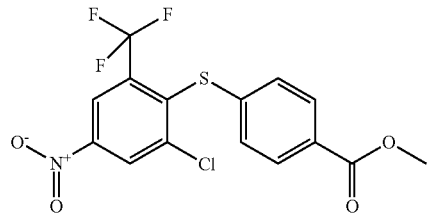 [SMILES: COC(=O)c1ccc(Sc2c(Cl)cc([N+](=O)[O-])cc2C(F)(F)F)cc1]

In a 250-mL round-bottomed flask, 1-chloro-2-fluoro-5-nitro-3-(trifluoromethyl)benzene (1.5 g, 6.16 mmol, Eq: 1.00), methyl 4-mercaptobenzoate (1.1 g, 6.54 mmol, Eq: 1.06) and potassium carbonate (851 mg, 6.16 mmol, Eq: 1.00) were combined with N,N-dimethylformamide (25 mL) to give a light brown suspension. The reaction mixture was heated at 100° C. for 7 hours. After this time, the reaction mixture was cooled room temperature. The reaction mixture was partitioned between water and ethyl acetate. The organic phase was dried (magnesium sulfate), filtered, then concentrated. The crude product (brown oil) was loaded directly onto a 120 gram ISCO column. Flash chromatography afforded 5 product bands. The second eluting band was the desired product by 1H NMR. Obtained 1.0 g (41.4%) of 4-(2-chloro-4-nitro-6-(trifluoromethyl)phenylthio)benzoate as a yellow solid.

methyl 4-(4-amino-2-chloro-6-(trifluoromethyl)phenylthio)benzoate

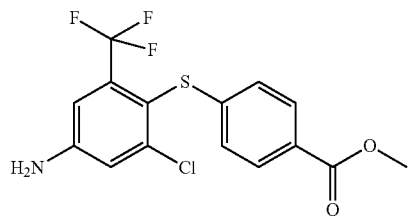 [SMILES: COC(=O)c1ccc(Sc2c(Cl)cc(N)cc2C(F)(F)F)cc1]

In a 500-mL round-bottomed flask, methyl 4-(2-chloro-4-nitro-6-(trifluoromethyl)phenylthio)benzoate (1.0 g, 2.55 mmol, Eq: 1.00), iron (713 mg, 12.8 mmol, Eq: 5) and ammonium chloride (1.37 g, 25.5 mmol, Eq: 10) were combined with methanol (8.5 mL) to give a yellow suspension. Water was added. The reaction mixture was heated at 100° C. for 2 hr. After this time, the reaction mixture was a brick-red suspension. The reaction mixture was cooled to room temperature, then filtered. About half of the methanol was evaporated off. The resulting solution was partitioned between saturated aqueous sodium bicarbonate and ethyl acetate. The organic phase was dried (magnesium sulfate) filtered, and concentrated to afford 0.790 g (85.5%) of methyl 4-(4-amino-2-chloro-6-(trifluoromethyl)phenylthio)benzoate as a yellow oily solid. This product was used without further purification.

4-(2-chloro-4-isothiocyanato-6-trifluoromethylphenylsulfanyl)benzoic acid methyl ester

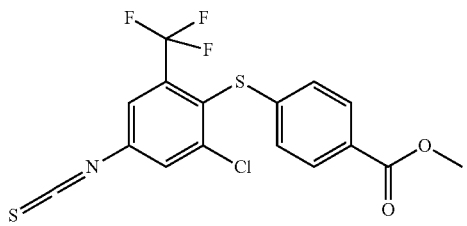 [SMILES: COC(=O)c1ccc(Sc2c(Cl)cc(N=CC=S)cc2C(F)(F)F)cc1]

Added dichloromethane (30 mL) and 1,1'-thiocarbonyldiimidazole (0.57 g, 3.2 mmol, Eq: 1.45) to the 100-mL round-bottomed flask containing methyl 4-(4-amino-2-chloro-6-(trifluoromethyl)phenylthio)benzoate (800 mg, 2.21 mmol, Eq: 1.00). Stirred at room temperature for 1 h; took a TLC in 1:3 ethyl acetate/hexanes: appeared only starting material was present. Stirred for another 2 h, took a TLC and still starting material Stirred overnight (18 h). Attempted to recover starting material. Diluted with dichloromethane and concentrated onto Celite. Purified using a 40 g silica gel column on an Intelliflash 280; collected peaks only in 28 mL fractions at 53 mL/min; equilibrated with 10% ethyl acetate/hexanes; dry loaded; eluted 2 min with 10% ethyl acetate/hexanes; increased from 10-30% dichloromethane/hexanes over 8 min; held at 30% for 2 min; increased from 30-50% over 8 min. Obtained 379.7 mg (42%) of 4-(2-chloro-4-isothiocyanato-6-trifluoromethylphenylsulfanyl)benzoic acid methyl ester as a yellow viscous oil, which partially solidified overnight; no starting material was recovered only product.

methyl 4-(2-chloro-4-((cyanoimino)(methylthio)methylamino)-6-(trifluoromethyl)phenylthio)-benzoate

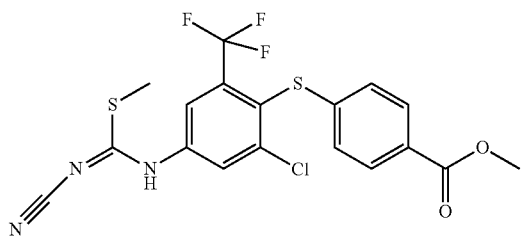 [SMILES: COC(=O)c1ccc(Sc2c(Cl)cc(N/C(=N\C#N)SC)cc2C(F)(F)F)cc1]

Charged cyanamide (1.6 g, 38.1 mmol) into a 100-mL round-bottomed flask; added 0.5 M sodium methoxide (37.5 mL, 17.75 mmol) and stirred at room temperature for 30 min. Meanwhile, added toluene (3.8 mL) and methanol (4 mL) to the 100-mL round-bottomed flask that contained 4-(2-chloro-4-isothiocyanato-6-trifluoromethylphenylsulfanyl)benzoic acid methyl ester (380 mg, 941 μmol. Eq: 1.00). Added the cyanamide mixture (2.45 mL, 1.22 mmol, Eq: 1.3) to the starting material via syringe. Stirred at room temperature and monitored by TLC: 1:3 ethyl acetate/hexanes; after 2.5 h the starting material had been consumed Added iodomethane (272 mg, 120 μL, 1.92 mmol, Eq: 2.04) and stirred at room temperature. After 1.5 h took a TLC in 100% ethyl acetate: reaction was complete. Transferred the reaction mixture to a 250-mL round-bottomed flask and concentrated onto Celite. Purified using a 40 g silica gel column on an Intelliflash 280; collected peaks only in 28 mL fractions at 35 mL/min; equilibrated with 50% ethyl acetate/hexanes; dry loaded; eluted 2 min with 50% ethyl acetate/hexanes; increased from 50-100% ethyl acetate/hexanes over 20 min. Obtained 197 mg (45.5%) of methyl 4-(2-chloro-4-((cyanoimino)(methylthio)methylamino)-6-(trifluoromethyl)phenylthio)benzoate as a white solid.

4-[4-(5-Amino-1H-[1,2,4]triazol-3-ylamino)-2-chloro-6-trifluoromethyl-phenylsulfanyl]-benzoic acid methyl ester (Compound 15)

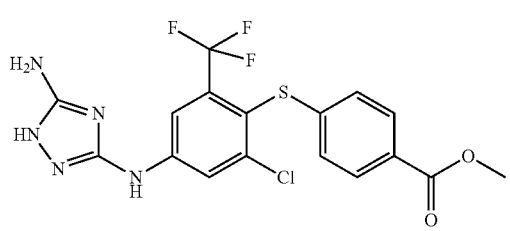 [SMILES: COC(=O)c1ccc(Sc2c(Cl)cc(Nc3n[nH]c(N)n3)cc2C(F)(F)F)cc1]

Added ethanol (10 mL) and hydrazine (102 mg, 100 μL, 3.19 mmol, Eq: 7.44) to the 100-mL round-bottomed flask containing methyl 4-(2-chloro-4-((cyanoimino)(methylthio)methylamino)-6-(trifluoromethyl)phenylthio)benzoate (197 mg, 428 μmol, Eq: 1.00). Refluxed for 1 h; confirmed completion of the reaction by TLC in 100% ethyl acetate and LC/MS. Concentrated the reaction mixture in vacuo. Dried in a vacuum oven at 70° C. under high vacuum. Obtained 184.5 mg (97%) of 4-[4-(5-Amino-1H-[1,2,4]triazol-3-ylamino)-2-chloro-6-trifluoromethyl-phenylsulfanyl]-benzoic acid methyl ester as an off-white solid. MS calcd. for C17H13ClF3NO2S [(M+H)+] 444.0, obsd. 408.8.

N*3*-[3,5-Dichloro-4-(4-methoxy-phenylsulfanyl)-phenyl]-1H-[1,2,4]triazole-3,5-diamine (Compound 16)

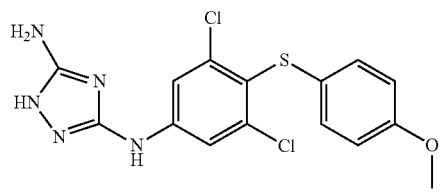

(2,6-dichloro-4-nitrophenyl)(4-methoxyphenyl)sulfane

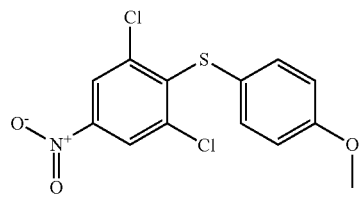 [SMILES: COc1ccc(Sc2c(Cl)cc([N+](=O)[O-])cc2Cl)cc1]

In a 250-mL round-bottomed flask, 4-methoxybenzenethiol (1.00 g, 633 µl 7.14 mmol, Eq: 1.00), 1,3-dichloro-2-fluoro-5-nitrobenzene (1.5 g, 7.14 mmol, Eq: 1.00) and potassium carbonate (990 mg, 7.16 mmol, Eq: 1.00) were combined with N,N-dimethylformamide (20 mL) to give a yellow suspension. The reaction mixture was stirred overnight at room temperature. In the morning TLC was consistent with the reaction having reached completion. The reaction mixture was poured into water to give a yellow cloudy suspension. This suspension was extracted with ethyl acetate. The organic phase was dried over Sodium sulfate, filtered, then concentrated to give a brown oil which was loaded directly onto a 120 gram silica gel column. Flash chromatography 5-15% EtOAC in hexanes was used to purify the product, however, this purification was not very successful. The fractions containing the product were concentrated. 1H NMR showed that the product was consistent with product with only a small impurity. Obtained 2.2 g (93.3%) of (2,6-dichloro-4-nitrophenyl)(4-methoxyphenyl) sulfane as a yellow oil.

3,5-dichloro-4-(4-methoxyphenylthio)aniline

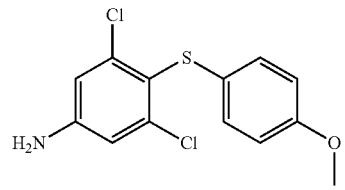 [SMILES: COc1ccc(Sc2c(Cl)cc(N)cc2Cl)cc1]

Charged iron (1.78 g, 31.8 mmol, Eq: 5.0), ammonium chloride (3.4 g, 63.6 mmol, Eq: 10.0), and methanol (80 mL) into the 500-mL round-bottomed flask containing (2,6-dichloro-4-nitrophenyl)(4-methoxyphenyl)sulfane (2.1 g, 6.36 mmol, Eq: 1.00). Heated at reflux; after 2 h the reaction was complete by TLC (1:3 ethyl acetate/hexanes) and LC/MS. Cooled the mixture to room temperature, then filtered through a bed of celite rinsing with a large amount of methanol. Concentrated the filtrate in vacuo. Added ethyl acetate to the residue and filtered off the solids. Concentrated the filtrate and obtained 1.87 g (98%) of 3,5-dichloro-4-(4-methoxyphenylthio)aniline as a dark brown oil that solidified over time.

1,3-dichloro-5-isothiocyanato-2-(4-methoxyphenylsulfanyl)benzene

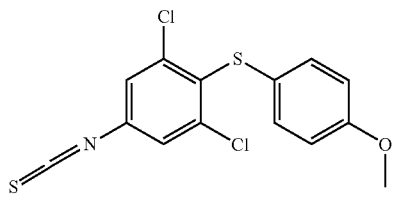 [SMILES: COc1ccc(Sc2c(Cl)cc(N=CC=S)cc2Cl)cc1]

Charged dichloromethane (50 mL) and 1,1'-thiocarbonyldiimidazole (1.44 g, 8.1 mmol, Eq: 1.3) to the 250-mL round-bottomed flask containing 3,5-dichloro-4-(4-methoxyphenylthio)aniline (1.87 g, 6.23 mmol, Eq: 1.00). Stirred at room temperature. Monitored the reaction by TLC (1:3 ethyl acetate/hexanes). Stirred over the weekend. Diluted the reaction with dichloromethane, added Celite, and concentrated. Purified using a 40 g silica gel column on an Intelliflash 280; collected peaks only in 28 mL fractions at 53 mL/min; equilibrated with hexanes; dry loaded; eluted 2 min with hexanes; increased from 0-25% dichloromethane/hexanes over 10 min; held at 25% for 5.5 min; stepped to 40% dichloromethane/hexanes and held for 5 min. Obtained 861 mg (40%) of 1,3-dichloro-5-isothiocyanato-2-(4-methoxyphenylsulfanyl)benzene as an orange oil.

(Z)-methyl N'-cyano-N-(3,5-dichloro-4-(4-methoxyphenylthio)phenyl)carbamimidothioate

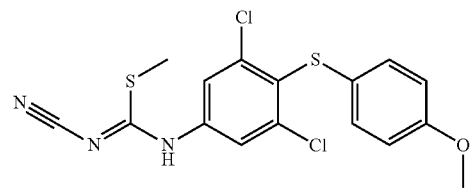 [SMILES: COc1ccc(Sc2c(Cl)cc(N/C(=N/C#N)SC)cc2Cl)cc1]

Combined cyanamide (440 mg, 10.5 mmol) and 0.5 M sodium methoxide (10.0 mL, 5.0 mmol). Then added some of the cyanamide mixture (6.04 mL, 3.02 mmol, Eq: 1.2) to a mixture of 1,3-dichloro-5-isothiocyanato-2-(4-methoxyphenylsulfanyl)benzene (861 mg, 2.52 mmol, Eq: 1.00) in methanol (15 mL) and toluene (3 mL). Stirred at room temperature. After 1 h TLC in 1:3 ethyl acetate/hexanes showed starting material consumed. Added iodomethane (714 mg, 315 µL, 5.03 mmol, Eq: 2.0) and stirred overnight. During the night solids precipitated out. Placed the reaction mixture in the freezer for 3 h. Filtered off the solids, rinsing with cold methanol, and air dried for 2 h. Obtained 729 mg (73%) of (Z)-methyl N'-cyano-N-(3,5-dichloro-4-(4-methoxyphenylthio)phenyl)carbamimidothioate as a yellow solid.

N*3*-[3,5-Dichloro-4-(4-methoxy-phenylsulfanyl)-phenyl]-1H-[1,2,4]triazole-3,5-diamine (Compound 16)

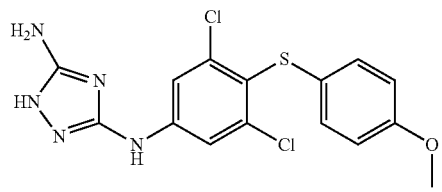 [SMILES: COc1ccc(Sc2c(Cl)cc(Nc3n[nH]c(N)n3)cc2Cl)cc1]

Added ethanol (15 mL) and hydrazine (292 mg, 0.286 mL, 9.11 mmol, Eq: 5.01) to the 50-mL round-bottomed flask containing (Z)-methyl N'-cyano-N-(3,5-dichloro-4-(4-methoxyphenylthio)phenyl)carbamimidothioate (725 mg, 1.82 mmol, Eq: 1.00). Heated at reflux for 30 min (during which time yellow solid dissolved, then white solids crashed out): TLC in 10% methanol/dichloromethane with 1% ammonium hydroxide showed that all the starting material had been consumed. Cooled to room temperature. Placed the reaction mixture in the freezer for ~2 h. Filtered off the solids, rinsing with cold ethanol. Air dried on the frit for 1 h. Obtained 596 mg (86%) of N*3*-[3,5-Dichloro-4-(4-methoxy-phenylsulfanyl)-phenyl]-1H-[1,2,4]triazole-3,5-diamine as a white fluffy solid. MS calcd. for C15H13Cl2N5OS [(M+H)+] 382.0, obsd. 381.9.

N*3*-[3-Chloro-4-(4-methoxy-phenylsulfanyl)-5-trifluoromethyl-phenyl]-1H-[1,2,4]triazole-3,5-diamine (Compound 17)

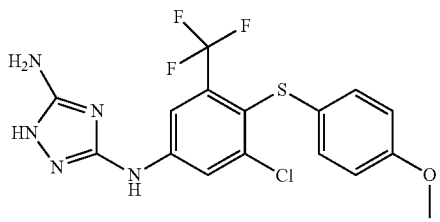 [SMILES: COc1ccc(Sc2c(Cl)cc(Nc3n[nH]c(N)n3)cc2C(F)(F)F)cc1]

2-chloro-4-nitro-6-(trifluoromethyl)phenyl)(4-methoxyphenyl)sulfane

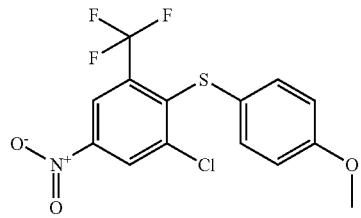 [SMILES: COc1ccc(Sc2c(Cl)cc([N+](=O)[O-])cc2C(F)(F)F)cc1]

In a 250-mL round-bottomed flask, 4-methoxybenzenethiol (1.00 g, 633 µl, 7.14 mmol, Eq: 1.00), 1,3-dichloro-2-fluoro-5-nitrobenzene (1.5 g, 7.14 mmol, Eq: 1.00) and potassium carbonate (990 mg, 7.16 mmol, Eq: 1.00) were combined with N,N-dimethylformamide (20 mL) to give a yellow suspension. The reaction mixture was stirred overnight at room temperature. In the morning TLC was consistent with the reaction having reached completion. The reaction mixture was poured into water to give a yellow cloudy suspension. This suspension was extracted with ethyl acetate. The organic phase was dried over sodium sulfate, filtered, then concentrated to give a brown oil which was loaded directly onto a 120 gram silica gel column. Flash chromatography 5-15% ethyl acetate in hexanes was used to purify the product, however, this purification was not very successful. The fractions containing the product were concentrated. 1H NMR showed that the product was consistent with product with only a small impurity. The product was sufficiently pure to take onto the next step. Obtained 1.87 g (83.5%) of 2-chloro-4-nitro-6-(trifluoromethyl)phenyl)(4-methoxyphenyl)sulfane.

3-chloro-4-(4-methoxyphenylthio)-5-(trifluoromethyl)aniline

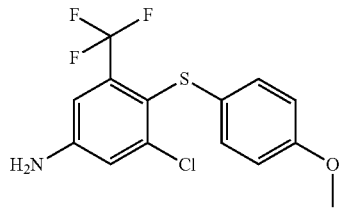 [SMILES: COc1ccc(Sc2c(Cl)cc(N)cc2C(F)(F)F)cc1]

Charged iron (1.44 g, 25.7 mmol, Eq: 5.0), Ammonium chloride (2.75 g, 51.4 mmol, Eq: 10.0), and methanol (80 mL) into the 500-mL round-bottomed flask containing (2-chloro-4-nitro-6-(trifluoromethyl)phenyl)(4-methoxyphenyl)sulfane (1.87 g, 5.14 mmol, Eq: 1.00). Heated at reflux; after 2 h the reaction was complete by TLC (1:3 ethyl acetate/hexanes) and LC/MS. Cooled the mixture to room temperature, then filtered through a bed of celite rinsing with a large amount of methanol. Concentrated the filtrate in vacuo. Added ethyl acetate to the residue and filtered off the solids. Concentrated the filtrate and obtained 3-chloro-4-(4-methoxyphenylthio)-5-(trifluoromethyl)aniline (1.32 g, 3.95 mmol, 76.9% yield) as a reddish-orange solid.

chloro-5-isothiocyanato-2-(4-methoxyphenylsulfanyl)-3-trifluoromethylbenzene

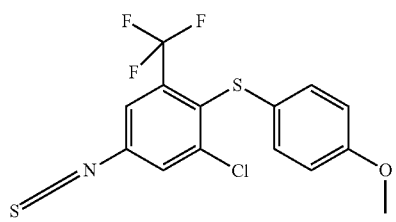 [SMILES: COc1ccc(Sc2c(Cl)cc(N=C=S)cc2C(F)(F)F)cc1]

Charged dichloromethane (50 mL) and 1,1'-thiocarbonyldiimidazole (916 mg, 5.14 mmol, Eq: 1.3) to the 250-mL round-bottomed flask containing 3-chloro-4-(4-methoxyphenylthio)-5-(trifluoromethyl)aniline (1.32 g, 3.95 mmol, Eq: 1.00). Stirred at room temperature. Monitored the reaction by TLC (1:3 ethyl acetate/hexanes) stirred over the weekend at room temperature, and TLC confirmed the reaction was complete. Diluted the reaction with dichloromethane, added Celite, and concentrated. Purified using a 40 g silica gel column on an Intelliflash 280; collected peaks only in 28 mL fractions at 53 mL/min; equilibrated with hexanes; dry loaded; eluted 2 min with hexanes; increased from 0-40% dichloromethane/hexanes over 18 min. Obtained 612 mg (41%) of 1-chloro-5-isothiocyanato-2-(4-methoxyphenylsulfanyl)-3-trifluoromethylbenzene as an orange oil.

59

(Z)-methyl N-3-chloro-4-(4-methoxyphenylthio)-5-(trifluoromethyl)phenyl-N'-cyanocarbamimidothioate

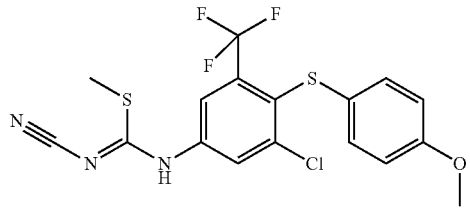 [SMILES: COc1ccc(Sc2c(Cl)cc(N/C(=N/C#N)SC)cc2C(F)(F)F)cc1]

Combined cyanamide (440 mg, 10.5 mmol) and 0.5 M sodium methoxide (10.0 mL, 5.0 mmol). Added the cyanamide mixture (3.91 mL, 1.95 mmol, Eq: 1.2) to a mixture of 1-chloro-5-isothiocyanato-2-(4-methoxyphenylsulfanyl)-3-trifluoromethylbenzene (612 mg, 1.63 mmol, Eq: 1.00) in methanol (10 mL) and toluene (2 mL) Stirred at room temperature. After 1 h TLC in 1:3 ethyl acetate/hexanes showed starting material consumed. Added iodomethane (462 mg, 204 µL, 3.26 mmol, Eq: 2.0) and stirred overnight. During the night solids precipitated out. Placed the reaction mixture in the freezer for 3 h. Filtered off the solids, rinsing with cold methanol, and air dried for 2 h. Obtained 412 mg (59%) of (Z)-methyl N-3-chloro-4-(4-methoxyphenylthio)-5-(trifluoromethyl)phenyl-N'-cyanocarbamimidothioate as a light yellow solid.

N*3*-[3-Chloro-4-(4-methoxy-phenylsulfanyl)-5-trifluoromethyl-phenyl]-1H-[1,2,4]triazole-3,5-diamine (Compound 17)

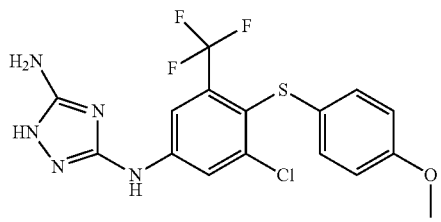 [SMILES: COc1ccc(Sc2c(Cl)cc(Nc3n[nH]c(N)n3)cc2C(F)(F)F)cc1]

Added ethanol (15 mL) and hydrazine (151 mg, 0.148 mL, 4.72 mmol, Eq: 5.00) to the 50-mL round-bottomed flask containing (Z)-methyl N-3-chloro-4-(4-methoxyphenylthio)-5-(trifluoromethyl)phenyl-N'-cyanocarbamimidothioate (407 mg, 942 µmol, Eq: 1.00). Stirred at room temperature for 40 min, then heated at reflux for 20 min: TLC in 10% methanol/dichloromethane with 1% ammonium hydroxide showed that all the starting material had been consumed. Cooled to room temperature. Removed the solvent in vacua. Obtained 367 mg (94%) of N*3*-[3-Chloro-4-(4-methoxy-phenylsulfanyl)-5-trifluoromethyl-phenyl]-1H-[1,2,4]triazole-3,5-diamine as a white solid. MS calcd. for C16H13ClF3N5OS [(M+H)+] 416.0, obsd. 415.9.

60

N*3*-[3,5-Dichloro-4-(4-methoxy-benzenesulfonyl)-phenyl]-1H-[1,2,4]triazole-3,5-diamine (Compound 18)

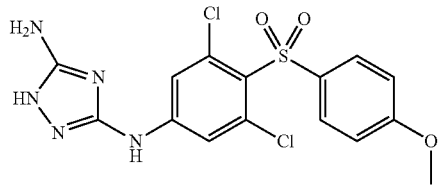 [SMILES: COc1ccc(S(=O)(=O)c2c(Cl)cc(Nc3n[nH]c(N)n3)cc2Cl)cc1]

Combined N3-(3,5-dichloro-4-(4-methoxyphenylthio)phenyl)-1H-1,2,4-triazole-3,5-diamine (compound 16) (150 mg, 392 µmol, Eq: 1.00), oxone (1.21 g, 1.96 mmol, Eq: 5.00), and methanol (5 mL) together in a 25-mL round-bottomed flask. Stirred overnight at room temperature open to the air. TLC in 10% methanol/dichloromethane with 1% ammonium hydroxide showed a new, more polar spot; LC/MS showed sulfoxide and starting material only. Transferred the reaction mixture to a seal tube and heated at 70° C. for 4 h. LC/MS showed sulfoxide and a very small sulfone peak. Heated overnight at 70° C. LC/MS showed slightly larger sulfone peak, but mostly sulfoxide still. Heated at 90° C. for 3 days: LC/MS showed proportionately more sulfone. Added more oxone (605 mg, 98 mmol, Eq: 2.5) and heated at 105° C., still only a small amount of sulfone. Decided to work-up: filtered off the solids, rinsing with methanol. The filtrate was concentrated and purified by prep-HPLC. Obtained 9.5 mg (6%) of N*3*-[3,5-Dichloro-4-(4-methoxy-benzenesulfonyl)-phenyl]-1H-[1,2,4]triazole-3,5-diamine as waxy, yellow solid. MS calcd. for C15H13Cl2N5O3S [(M+MeCN+H)+] 455.0, obsd. 454.8.

N*3*-[3,5-Dichloro-4-(4-methanesulfonyl-phenoxy)-phenyl]-1H-[1,2,4]triazole-3,5-diamine (Compound 19)

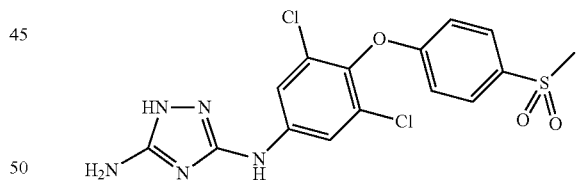

1,3-Dichloro-2-(4-methanesulfonyl-phenoxy)-5-nitro-benzene

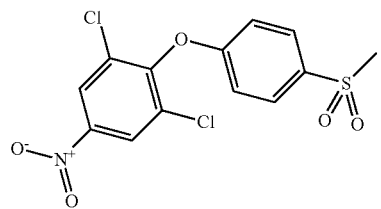 [SMILES: CS(=O)(=O)c1ccc(Oc2c(Cl)cc([N+](=O)[O-])cc2Cl)cc1]

To a stirred solution of 1,3-dichloro-2-fluoro-5-nitrobenzene (2.09 g, 10 mmol) in DMF (20 mL), was added K2CO3 (2.06 g, 15 mmol) and 4-(methylsulfonyl) phenol (1.72 g, 10 mmol). The reaction mixture was stirred at 110° C. for 3 hrs. The reaction was poured into water (100 mL), extracted with diethyl ether (3×25 mL) and dried with sodium sulfate. Evaporation of solvent gave 3.48 g (96%) of desired product as an off white solid.

1,3-Dichloro-2-(4-methanesulfonyl-phenoxy)-5-amino-benzene

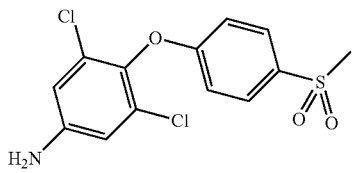 [SMILES: CS(=O)(=O)c1ccc(Oc2c(Cl)cc(N)cc2Cl)cc1]

A suspension of 1,3-Dichloro-2-(4-(methylsulfonyl)phenoxy)-5-nitrobenzene (3.4 g, 9.39 mmol) and 10% Pd/C (0.5 g, 0.47 mmol) in EtOAc (100 mL) was hydrogenated at 50 PSI for 3 hrs at rt. The reaction mixture was filtered and the filtrate was concentrated to give 3.02 g (97%) of desired product as a white solid. MS +m/z: 331.9 (M+H)+

$^1$H NMR (300 MHz, DMSO-$d_6$) δ ppm 3.19 (s, 3H) 5.74 (s, 2H) 6.56-7.22 (m, 4H) 7.89 (d, J=8.67 Hz, 2H)

(E)-Methyl N'-cyano-N-(3,5-dichloro-4-(4-(methylsulfonyl)phenoxy)phenyl)carbamimidothioate

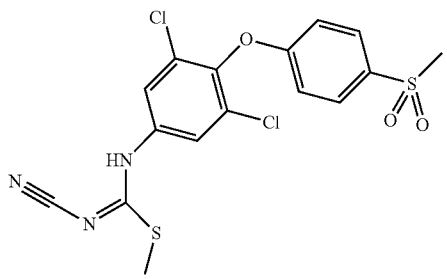 [SMILES: CS/C(=N/C#N)Nc1cc(Cl)c(Oc2ccc(S(C)(=O)=O)cc2)c(Cl)c1]

To a solution of 1,3-dichloro-2-(4-methanesulfonyl-phenoxy)-5-amino-benzene (332 mg, 1 mmol) in pyridine (5 mL), was added dimethyl cyanocarbonimidodithioate (146 mg, 1 mmol). The reaction mixture was heated at reflux for 3 hours. The solvent was removed by evaporation and the residue was chromatographed (methylene chloride) to give 242 mg (56%) of desired product as a brown solid. MS +m/z: 429.8 (M+H)+

N*3*-[3,5-Dichloro-4-(4-methanesulfonyl-phenoxy)-phenyl]-1H-[1,2,4]triazole-3,5-diamine (Compound 19)

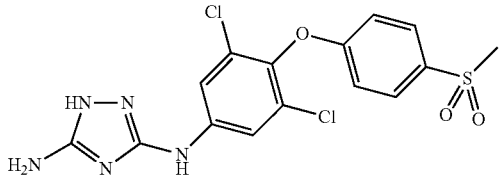 [SMILES: CS(=O)(=O)c1ccc(Oc2c(Cl)cc(Nc3n[nH]c(N)n3)cc2Cl)cc1]

To a solution of (E)-Methyl N'-cyano-N-(3,5-dichloro-4-(4-methylsulfonyl)phenoxy)phenyl) carbamimidothioate (240 mg, 0.558 mmol) in THF (4 mL) and methanol (2 mL), was added hydrazine (35.7 mg, 0.035 uL, 1.12 mmol). The reaction mixture was stirred overnight at room temperature. The solvent was removed and the residue was chromatographed on a combiflash machine (5% methanol/methylene chloride, then 5% methanol/EtOAc) to give 178 mg (77%) of desired product as a white solid. MS +m/z: 413.8 (M+H)+

$^1$H NMR (300 MHz, DMSO-$d_6$) δ ppm 3.20 (s, 3H) 6.02 (br. s, 2H) 7.07 (d, J=8.85 Hz, 2H) 7.67-8.00 (m, 4H) 9.29 (s, 1H) 11.32 (s, 1H)

N*3*-[3-Chloro-4-(4-methanesulfonyl-phenoxy)-5-trifluoromethyl-phenyl]-1H-[1,2,4]triazole-3,5-diamine (Compound 20)

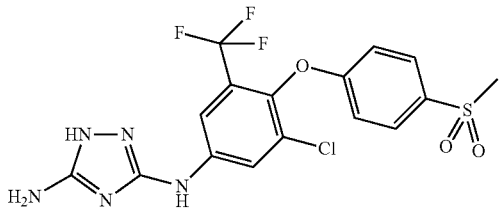 [SMILES: CS(=O)(=O)c1ccc(Oc2c(Cl)cc(Nc3n[nH]c(N)n3)cc2C(F)(F)F)cc1]

Chloro-2-(4-methanesulfonyl-phenoxy)-5-nitro-3-trifluoromethyl-benzene

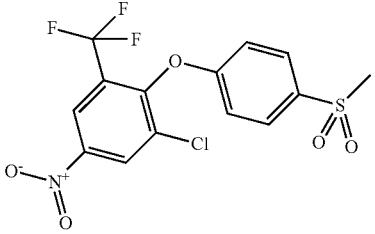 [SMILES: CS(=O)(=O)c1ccc(Oc2c(Cl)cc([N+](=O)[O-])cc2C(F)(F)F)cc1]

To a stirred solution of 1-chloro-2-fluoro-3-trifluoromethyl-5-nitrobenzene (1.42 g, 5.81 mmol) in DMF (20 mL), was added K2CO3 (2.06 g, 15 mmol) and 4-(methylsulfonyl) phenol (1.0 g, 5.81 mmol). The reaction mixture was stirred at 110° C. for 3 hrs. The reaction was poured into water (100 mL) and the mixture was extracted with toluene (3×25 mL) and dried with sodium sulfate. Evaporation of solvent gave 1.82 g (79%) of desired product as an off-white solid.

¹H NMR (300 MHz, DMSO-d₆) δ ppm 3.24 (s, 3H) 7.23 (d, J=8.85 Hz, 2H) 7.94 (d, J=8.85 Hz, 2H) 8.60 (d, J=2.45 Hz, 1H) 8.93 (d, J=2.45 Hz, 1H)

Chloro-2-(4-methanesulfonyl-phenoxy)-5-amino-3-trifluoromethyl-benzene

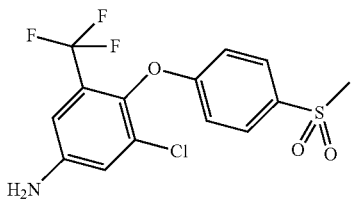 [SMILES: CS(=O)(=O)c1ccc(Oc2c(Cl)cc(N)cc2C(F)(F)F)cc1]

A suspension of 1-Chloro-2-(4-(methylsulfonyl)phenoxy)-5-nitro-3-(trifluoromethyl)benzene (1.8 g, 4.55 mmol) and Pd/C (10%, 120 mg, 0.115 mmol) in ethyl acetate (50 mL) was hydrogenated at 50 PSI for 3 hrs. The reaction mixture was filtered and the filtrate was concentrated to give 1.59 g (96%) of desired product as a white solid.

¹H NMR (300 MHz, DMSO-d₆) δ ppm 3.20 (s, 3H) 5.94 (s, 2H) 6.91-7.10 (m, 4H) 7.87 (d, J=8.85 Hz, 2H)

(E)-Methyl N-3-chloro-4-(4-(methylsulfonyl)phenoxy)-5-(trifluoromethyl)phenyl-N'-cyanocarbamimidothioate

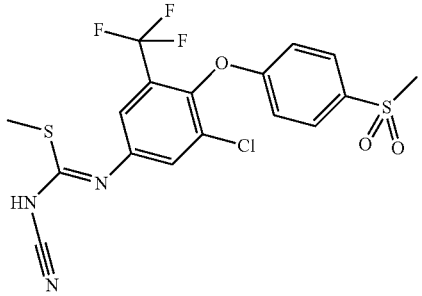

To a stirred solution of 3-chloro-4-(4-(methylsulfonyl)phenoxy)-5-(trifluoromethyl)aniline (182 mg, 0.50 mmol) in THF (4 mL), was added 1M potassium tert-butoxide in THF (0.50 mL, 0.50 mmol) drop wise. The reaction mixture was stirred at rt for 15 min, after which dimethyl cyanocarbonimidodithioate (73 mg, 0.50 mmol) was added, and the resulting mixture was stirred at rt for 2 hrs. The solvent was removed and the residue was chromatographed (100% methylene chloride gradient to 5% methanol/methylene chloride) to give 60 mg (26%) of desired product as an orange solid. MS +m/z: 463.63 (M+H)⁺

N*3*-[3-Chloro-4-(4-methanesulfonyl-phenoxy)-5-trifluoromethyl-phenyl]-1H-[1,2,4]triazole-3,5-diamine (Compound 20)

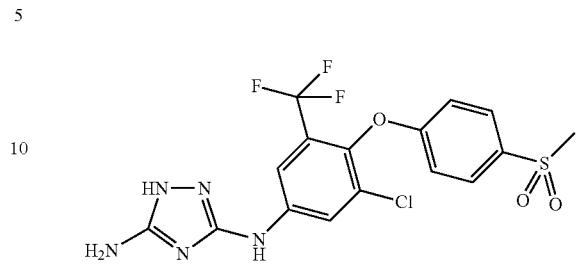

To a stirred solution of (Z)-methyl N-3-chloro-4-(4-(methylsulfonyl)phenoxy)-5-(trifluoromethyl)phenyl-N'-cyanocarbamimidothioate (60 mg, 0.129 mmol) in methanol (3 mL) at rt, was added hydrazine monohydrate (5 mg, 0.155 mmol). The reaction mixture was stirred for 3 hrs, after which the solvent was reduced to 1.5 mL and filtered through a membrane filter and then loaded on a HPLC. Collection of the desired peak gave the 11 mg (19%) of desired product as white solid. MS +m/z: 447.9 (M+H)⁺

¹H NMR (300 MHz, DMSO-d₆) δ ppm 3.20 (s, 12H) 6.05 (br. s, 2H) 7.07 (d, J=8.67 Hz, 2H) 7.88 (d, J=8.67 Hz, 2H) 7.95-7.98 (m, 1H) 8.10 (s, 1H) 9.47 (s, 1H) 11.38 (br. s, 1H)

N*5*-(3-Benzyloxy-5-chloro-phenyl)-1H-[1,2,4]triazole-3,5-diamine (Compound 21)

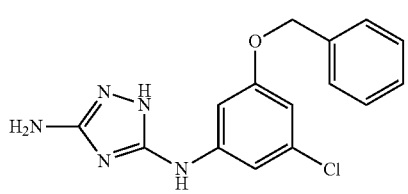 [SMILES: Nc1n[nH]c(Nc2cc(Cl)cc(OCc3ccccc3)c2)n1]

1-(benzyloxy)-3-chloro-5-isothiocyanatobenzene

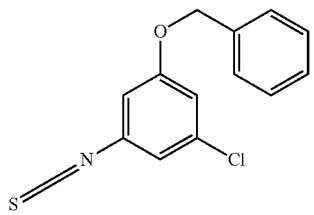 [SMILES: S=C=Nc1cc(Cl)cc(OCc2ccccc2)c1]

3-(benzyloxy)-5-chloroaniline (775 mg, 3.32 mmol) and thiocarbonyldiimidazole (887 mg, 4.97 mmol) were stirred overnight in a solution of CH₂Cl₂ (12 mL). 1-(Benzyloxy)-3-chloro-5-isothiocyanatobenzene (870 mg, 95%) was purified directly from the reaction mixture by column chromatography (8:1, hexane:EtOAc) as a brown oil.

(Z)-methyl 3-(benzyloxy)-5-chloro-N-cyanobenzimidate

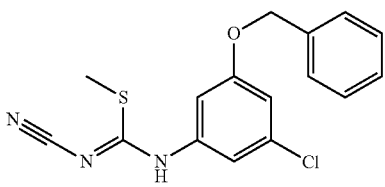 [SMILES: CS/C(=N\C#N)Nc1cc(Cl)cc(OCc2ccccc2)c1]

Sodium hydrogencyanamide (222 mg, 3.47 mmol) was added to a solution of 1-(benzyloxy)-3-chloro-5-isothiocyanatobenzene (896 mg, 6.3 mmol) in CH$_3$OH (20 mL). After stirring for 1.5 hours, iodomethane (395 μL, 6.31 mmol)) was added and the reaction mixture was stirred for 60 hours. All volatiles were then removed under reduced pressure and (Z)-methyl 3-(benzyloxy)-5-chloro-N-cyanobenzimidate (240 mg, 24%) was isolated by column chromatography (4:1 to 1:1 hexane: EtOAc).

N*5*-(3-Benzyloxy-5-chloro-phenyl)-1H-[1,2,4]triazole-3,5-diamine (Compound 21)

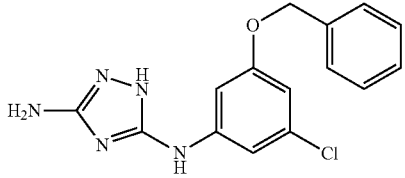 [SMILES: Nc1n[nH]c(Nc2cc(Cl)cc(OCc3ccccc3)c2)n1]

(Z)-methyl 3-(benzyloxy)-5-chloro-N-cyanobenzimidate (85 mg, 0.28 mmol) and hydrazine (200 μL, 6.37 mmol) in ethanol (2 mL) were heated to 85° C. for 16 hours. After cooling, all volatiles were removed under reduced pressure to yield a solid from which N*5*-(3-benzyloxy-5-chloro-phenyl)-1H-[1,2,4]triazole-3,5-diamine (33 mg, 37%) was isolated as a white solid by column chromatography (10% CH$_3$OH in CH$_2$Cl$_2$). MH+=316.0

N3-(3-chloro-4-(phenylthio)phenyl)-1H-1,2,4-triazole-3,5-diamine (Compound 22)

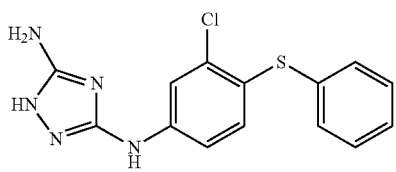 [SMILES: Nc1nc(Nc2ccc(Sc3ccccc3)c(Cl)c2)n[nH]1]

2-Chloro-4-nitro-1-phenylsulfanyl-benzene

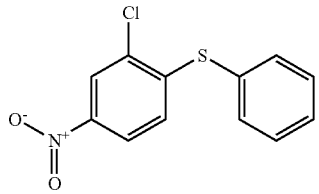 [SMILES: O=[N+]([O-])c1ccc(Sc2ccccc2)c(Cl)c1]

In a 250 mL round-bottom flask, 2-chloro-1-fluoro-4-nitrobenzene (4.0 g, 22.8 mmol, Eq: 1.00), thiophenol (2.34 mL, 22.8 mmol, Eq: 1.00) and potassium carbonate (6.3 g, 45.6 mmol, Eq: 2.0) were combined with DMF (45.6 mL) to give a light brown suspension. The reaction mixture was heated at 100° C. overnight. In the morning, the reaction mixture was cooled to room temperature and partitioned between water and ethyl acetate. The organic phase was dried (MgSO$_4$), filtered, and concentrated to afford a brown oil. The crude product was dissolved in methylene chloride, and this solution was concentrated over silica gel. The silica gel supported crude product was loaded onto a 220 gram SiliCycle column. Flash chromatography (5-10% ethyl acetate-hexanes) afforded 2-chloro-4-nitro-1-phenylsulfanyl-benzene (7.5 g, 100%).

3-Chloro-4-(phenylthio)aniline

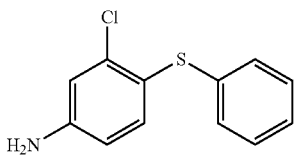 [SMILES: Nc1ccc(Sc2ccccc2)c(Cl)c1]

In a 250 mL round-bottom flask, 2-chloro-4-nitro-1-phenylsulfanyl-benzene (3.31 g, 12.5 mmol, Eq: 1.00), iron (3.48 g, 55.85 mmol, Eq: 5.0) and ammonium chloride (6.66 g, 53.49 mmol, Eq: 10) were combined with methanol (33 mL) to give a light brown suspension. Water (16.6 mL) was added, and the reaction mixture became a milky-white suspension. The reaction mixture was refluxed for 6 hours. The reaction mixture was filtered, and concentrated to remove most of the methanol. The resulting crude suspension was extracted with ethyl acetate. The organic phase was dried (MgSO$_4$), filtered, and concentrated to give 3-chloro-4-(phenylthio)aniline (2.47 g, 44%) as a slightly tan oil.

(2-Chloro-4-isothiocyanatophenyl)(phenyl)sulfane

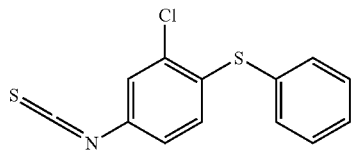 [SMILES: S=CC=Nc1ccc(Sc2ccccc2)c(Cl)c1]

In a 250 mL round-bottom flask, thiophosgene (884 μL, 11.5 mmol, Eq: 1.1) and calcium carbonate (1.05 g, 10.5 mmol, Eq: 1.00) were combined with dichloromethane (37.4 mL) and water at 0° C. to give a yellow suspension. The reaction mixture was stirred at 0° C. under argon for ten minutes. A mixture of 3-chloro-4-(phenylthio)aniline (2.47 g, 10.5 mmol, Eq: 1.00) in methylene chloride (5 mL) was added dropwise to the cold suspension via a syringe. The reaction mixture was stirred over four hours, slowly warming to room temperature. The reaction mixture was neutralized with 1.0 N aqueous HCl, and the resulting mixture was extracted with methylene chloride. The organic phase was dried over MgSO$_4$, and concentrated onto silica gel. The silica gel supported crude product was loaded onto a 200 g SiliCycle column. Flash chromatography 0%-5% ethyl acetate-hexanes afforded (2-chloro-4-isothiocyanatophenyl)(phenyl)sulfane (1.9 g, 65%) as a clear oil.

(Z)-methyl N-3-chloro-4-(phenylthio)phenyl-M-cyanocarbamimidothioate

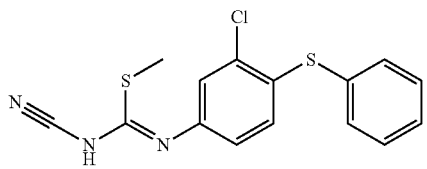 [SMILES: CS/C(=N\c1ccc(Sc2ccccc2)c(Cl)c1)NC#N]

Cyanamide (150 mg, 3.56 mmol, Eq: 1.1) was added to a 50 mL round-bottom flask while purging with argon. A 0.5 M solution of sodium methoxide in methanol (1.22 mL, 3.95 mmol, Eq: 1.2) was added at room temperature. The reaction mixture was then stirred for 15 minutes. Separately, (2-chloro-4-isothiocyanatophenyl)(phenyl)sulfane (0.9 g, 3.24 mmol, Eq: 1.00) was combined with methanol (13 mL) with stirring. The cyanamide mixture was transferred to the starting material mixture via a syringe. The resulting mixture was stirred for a total of 1 hour, then iodomethane (0.304 mL, 4.86 mmol, Eq: 1.5) was added. The reaction mixture was stirred at room temperature overnight. The mixture was then diluted with methylene chloride and methanol. The resulting solution was concentrated onto silica gel. The silica gel-supported crude product was loaded onto a 200 g silica gel column. Flash chromatography (100% hexanes) afforded (Z)-methyl N-3-chloro-4-(phenylthio)phenyl-N'-cyanocarbamimidothioate (240 mg, 22%) as a white solid.

N3-(3-chloro-4-(phenylthio)phenyl)-1H-1,2,4-triazole-3,5-diamine (Compound 22)

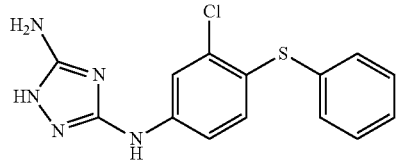 [SMILES: Nc1nc(Nc2ccc(Sc3ccccc3)c(Cl)c2)n[nH]1]

In a 250 mL round-bottom flask, (Z)-methyl N-3-chloro-4-(phenylthio)phenyl-N-cyanocarbamimidothioate (240 mg, 719 μmol, Eq: 1.00) was combined with ethanol (10 mL) to give a white suspension. Hydrazine (226 μL, 7.19 mmol, Eq: 10) was added. The reaction mixture was heated at reflux for 1 hour. The reaction mixture was concentrated, giving an oily foam-like substance. This product was dissolved in 15% methanol-chloroform, and the solution filtered through a small filter plug. The liquid filtrate was concentrated down to afford N3-(3-chloro-4-(phenylthio)phenyl)-1H-1,2,4-triazole-3,5-diamine as a brittle solid. MS cald. for $C_{14}H_{12}ClN_5S$ [(M+H)$^+$]: 318, obsd. 318.0.

N3-(3-chloro-4-(phenylsulfonyl)phenyl)-1H-1,2,4-triazole-3,5-diamine (Compound 23)

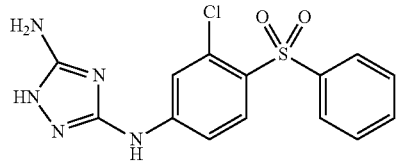 [SMILES: Nc1nc(Nc2ccc(S(=O)(=O)c3ccccc3)c(Cl)c2)n[nH]1]

(2-Chloro-4-nitrophenyl)(phenyl)sulfone

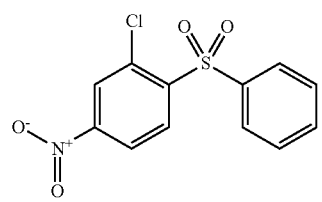 [SMILES: O=[N+]([O-])c1ccc(S(=O)(=O)c2ccccc2)c(Cl)c1]

In a 250 mL round-bottomed flask, 2-chloro-4-nitro-1-phenylsulfanyl-benzene (4.126 g, 15.5 mmol, Eq: 1.00) was combined with methylene chloride (100 mL) to give a yellow solution. This mixture was cooled to 0° C. in an ice water bath. m-Chloroperoxybenzoic acid (10.7 g, 62.1 mmol, Eq: 4.0) was added scoopwise. The reaction mixture was stirred overnight, with slow warming to room temperature. In the morning, the reaction mixture was washed with saturated aqueous sodium sulfite, then aqueous sodium bicarbonate. The organic phase was dried over MgSO$_4$, filtered, and concentrated to afford a white solid. The crude product was loaded onto silica gel. The silica gel supported crude product was loaded onto a 200 g silacycle column. Flash chromatography (40%-60% ethyl acetate-hexanes) provided (2-chloro-4-nitrophenyl)(phenyl)sulfone (2.03 g, 44%) as a white crystalline solid.

3-Chloro-4-(phenylsulfonyl)aniline

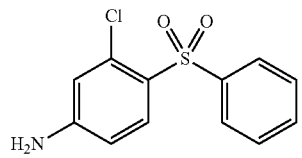 [SMILES: Nc1ccc(S(=O)(=O)c2ccccc2)c(Cl)c1]

In a 250 mL round-bottom flask, (2-chloro-4-nitrophenyl)(phenyl)sulfone (2.03 g, 6.82 mmol, Eq: 1.00), iron (1.9 g, 34.1 mmol, Eq: 5.0) and ammonium chloride (3.65 g, 98.2 mmol, Eq: 10) were combined with methanol (22.7 mL) to give a light brown suspension. Water (11.4 mL) was added, and the reaction mixture became a milky-white suspension. The reaction mixture was refluxed for 6 hours. After only 20 minutes, the reaction mixture was rust-colored. After 6 hours heating at reflux, the reaction mixture was cooled to room temperature. The mixture was filtered, and concentrated to remove most of the methanol. The resulting crude suspension was extracted with ethyl acetate. The organic phase was dried (MgSO$_4$), filtered, and concentrated to give 3-chloro-4-(phenylsulfonyl)aniline (1.8 g, 99%) as a white crystalline solid.

2-Chloro-4-isothiocyanato-1-(phenylsulfonyl)benzene

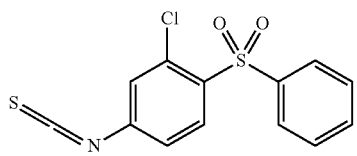 [SMILES: O=S(=O)(c1ccccc1)c1ccc(N=CC=S)cc1Cl]

In a 250 mL round-bottom flask, thiophosgene (567 µL, 7.4 mmol, Eq: 1.1) and calcium carbonate (0.673 g, 6.72 mmol, Eq: 1.00) were combined with dichloromethane (34 mL) and water (24 mL) at 0° C. to give a yellow suspension. The reaction mixture was stirred at 0° C. under argon for ten minutes. A mixture of 3-chloro-4-(phenylsulfonyl)aniline (1.8 g, 6.72 mmol, Eq: 1.00) in methylene chloride (5 mL) was added dropwise to the cold suspension via a syringe. The reaction mixture was stirred over four hours, being slowly allowed to warm to room temperature. The reaction mixture was neutralized with 1.0 N aqueous HCl, and then extracted with methylene chloride. The organic phase was dried over MgSO$_4$, and concentrated onto silica gel. The silica gel supported crude product was loaded onto a 200 g silicylce column. Flash chromatography (15%-40% ethyl acetate-hexane) afforded 2-chloro-4-isothiocyanato-1-)phenylsulfonyl)benzene (1.14 g, 55%) as a white crystalline solid.

(Z)-Methyl N-3-chloro-4-(phenylsulfonyl)phenyl-N'-cyanocarbamimidothioate

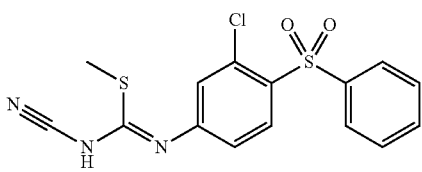 [SMILES: CS/C(=N\c1ccc(S(=O)(=O)c2ccccc2)c(Cl)c1)NC#N]

A 50 mL round-bottom flask was charged with cyanamide (170 mg, 4.03 mmol, Eq: 1.1) and a 0.5 M solution of sodium methoxide in methanol (8.1 mL, 4.05 mmol, Eq: 1.2), and this solution was stirred for 15 minutes. Separately, 2-chloro-4-isothiocyanato-1-)phenylsulfonyl)benzene (1.136 g, 3.67 mmol, Eq: 1.00) and methanol (14.7 mL) were combined. The cyanamide mixture was transferred to the starting material mixture via syringe at room temperature. The mixture became homogeneous after a short time of stirring. After stirring for one hour at room temperature, iodomethane (0.794 g, 0.350 mL, 5.6 mmol, Eq: 1.5) was added and the reaction mixture was stirred overnight at room temperature. The reaction mixture was diluted with a 9:1 mixture methylene chloride and methanol, and the solution was concentrated onto silica gel. The silica gel supported crude product was loaded onto a 120 gram silica gel column. Flash chromatography (25%-40% ethyl acetate-hexanes) was used to isolate (Z)-methyl N-3-chloro-4-(phenylsulfonyl)phenyl-N'-cyanocarbamimidothioate (84 mg, 6.3%) as a white solid.

N3-(3-chloro-4-(phenylsulfonyl)phenyl)-1H-1,2,4-triazole-3,5-diamine (Compound 23)

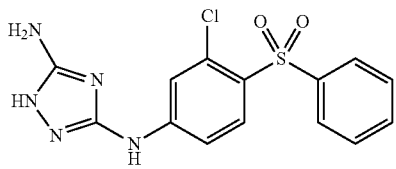 [SMILES: Nc1nc(Nc2ccc(S(=O)(=O)c3ccccc3)c(Cl)c2)n[nH]1]

In a 200 mL round-bottomed flask, (Z)-methyl N-3-chloro-4-(phenylsulfonyl)phenyl-N-cyanocarbamimidothioate (84 mg, 230 µmol, Eq: 1.00) and hydrazine (79 µL, 2.51 mmol, Eq: 11.0) were combined with ethanol (3.5 mL) to give a colorless solution. The reaction mixture was refluxed for 1 hour. The reaction mixture was concentrated down on the rotary evaporator. The crude product was a slightly yellow oil which was dissolved in 4:1 methylene chloride-methanol. This solution was carefully filtered. The filtrate was dried down to give N3-(3-chloro-4-(phenylsulfonyl)phenyl)-1H-1,2,4-triazole-3,5-diamine as a brittle off-white powder. MS cald for $C_{14}H_{12}ClN_5O_2S$ [(M+H)$^+$]: 350, obsd. 349.9.

N3-(3-chloro-4-(phenylthio)phenyl)-N3-methyl-1H-1,2,4-triazole-3,5-diamine (Compound 24)

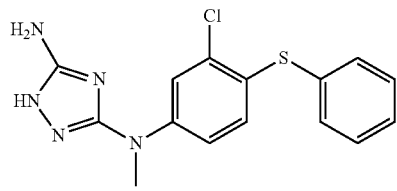

(Z)-methyl N-3-chloro-4-(phenylthio)phenyl-M-cyano-N-methylcarbamimidothioate

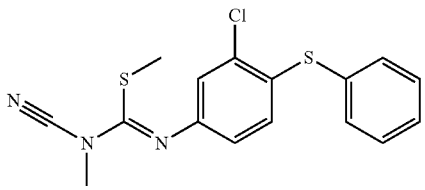 [SMILES: CS/C(=N\c1ccc(Sc2ccccc2)c(Cl)c1)N(C)C#N]

In a 50 mL round-bottomed flask, (Z)-methyl N-3-chloro-4-(phenylthio)phenyl-N'-cyanocarbamimidothioate (53 mg, 159 µmol, Eq: 1.00) was combined with DMF (1.59 mL) to give a colorless solution. This mixture was cooled to 0° C., then sodium hydride (60% suspension in oil, 6.98 mg, 175 µmol, Eq: 1.1) was added. The reaction mixture was stirred at 0° C. for 15 minutes, then methyl iodide (9.9 µL, 0.159 µmol) was added. The reaction mixture was slowly warmed to room temperature and then stirred at room temperature over 48 hours. The reaction mixture was quenched with water, and extracted with ethyl acetate. The organic phase was dried over MgSO$_4$, filtered, and concentrated in vacuo. The crude product was dissolved in methylene chloride, and then concentrated over silica gel. The silica gel supported crude product was loaded onto a 35 gram SiliCycle column. Flash chromatography (0%-15% ethyl acetate in hexanes) afforded the product (27 mg, 50%) as a clear oil.

N3-(3-chloro-4-(phenylthio)phenyl)-N3-methyl-1H-1,2,4-triazole-3,5-diamine (Compound 24)

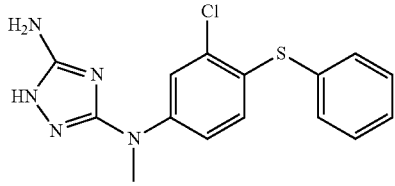 [SMILES: CN(c1ccc(Sc2ccccc2)c(Cl)c1)c1n[nH]c(N)n1]

In a 50 mL round-bottomed flask, (Z)-methyl N-3-chloro-4-(phenylthio)phenyl-N-cyano-N-methylcarbamimidothioate (27.6 mg, 79.3 µmol, Eq: 1.00) and hydrazine (50 µL, 1.59 mmol, Eq: 20.1) were combined with ethanol (2.5 mL) to give a white suspension. The reaction mixture was heated at reflux for 2 hours. The reaction mixture was concentrated. Preparatory reverse-phase LC purification provided N3-(3-chloro-4-(phenylthio)phenyl)-N3-methyl-1H-1,2,4-triazole-3,5-diamine (9 mg, 98%). MS cald. for $C_{15}H_{14}ClN_5S$ [(M+H)$^+$]: 332, obsd. 331.9.

Example 2

Procedure E

N*3*-(3-Chloro-5-phenoxy-phenyl)-1H-[1,2,4]triazole-3,5-diamine (Compound 25)

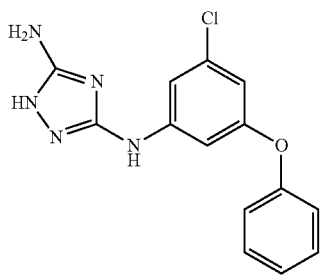 [SMILES: Nc1nc(Nc2cc(Cl)cc(Oc3ccccc3)c2)n[nH]1]

1-chloro-3-chloro-5-phenoxybenzene

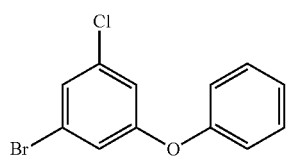

In a 250 mL round-bottomed flask, 3-bromo-5-chlorophenol (2 g, 9.64 mmol, Eq: 1.00), phenylboronic acid (2.35 g, 19.3 mmol, Eq: 2.00) and triethylamine (9.76 g, 96.4 mmol, Eq: 10.00) were combined with CH$_2$Cl$_2$ (100 ml) to give a colorless solution. Powdered 4A molecular sieves (200 mg) and copper(II) acetate (2.63 g, 14.5 mmol, Eq: 1.50) were added. The reaction was stirred at room temperature for 3 hours. Filtered out the solid, filtrate was evaporated in vacuo. The compound was isolated by column chromatography (Hexanes/EtOAc=70/30) to give the product 550 mg (20%).

5-Bromo-1-(4-methoxy-benzyl)-3-nitro-1H-[1,2,4]triazole

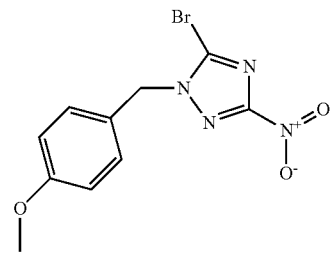 [SMILES: COc1ccc(Cn2nc([N+](=O)[O-])nc2Br)cc1]

In a 250 mL round-bottomed flask, 5-bromo-3-nitro-1H-1,2,4-triazole (12 g, 62.2 mmol, Eq: 1.00), 1-(chloromethyl)-4-methoxybenzene (9.74 g, 62.2 mmol, Eq: 1) and N-ethyl-N-isopropylpropan-2-amine (16.1 g, 124 mmol, Eq: 2) were combined with acetonitrile (100 ml) to give a light yellow solution. Potassium iodide (5.16 g, 31.1 mmol, Eq: 0.5) was added. The reaction mixture was heated to reflux for 2 hours. The reaction mixture was cooled and diluted with EtOAc (100 mL), washed with H$_2$O (50 mL) and brine (50 mL). The organic layer was dried over anhydrous MgSO$_4$, filtered and volatiles were removed under reduced pressure to yield an oil from which the compound was isolated by column chromatography (Hexanes/EtOAc=70/30) to product 7.8 g (40%).

Bis-(4-methoxy-benzyl)-[2-(4-methoxy-benzyl)-5-nitro-2H-[1,2,4]triazol-3-yl]-amine

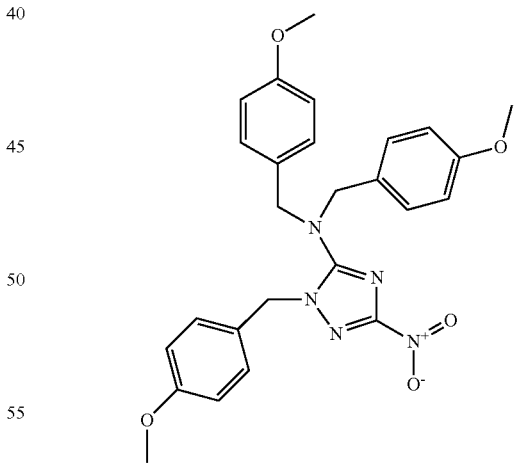

In a 10 mL sealed tube, 5-bromo-1-(4-methoxybenzyl)-3-nitro-1H-1,2,4-triazole (5.48 g, 17.5 mmol, Eq: 1.00) and bis(4-methoxybenzyl)amine (4.5 g, 17.5 mmol, Eq: 1.00) were combined, the mixture was heated to 150° C. for overnight. Cool the reaction down, added CH$_2$Cl$_2$ (50 mL) washed with H$_2$O (50 mL) and brine (50 mL), the organic layer was dried over anhydrous MgSO$_4$, filtered and volatiles were removed under reduced pressure to afford the crude product 8.3 g (97% crude). MH+ 490.3

1,N*5*,N*5*-Tris-(4-methoxy-benzyl)-1H-[1,2,4]triazole-3,5-diamine

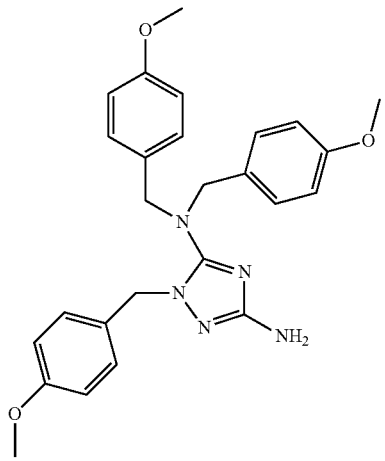 [SMILES: COc1ccc(CN(Cc2ccc(OC)cc2)c2nc(N)nn2Cc2ccc(OC)cc2)cc1]

In a 100 mL round bottle, bis-(4-methoxy-benzyl)-[2-(4-methoxy-benzyl)-5-nitro-2H-[1,2,4]triazol-3-yl]amine (530 mg, 1.08 mmol, Eq: 1.00) and zinc (354 mg, 5.41 mmol, Eq: 5.00) were combined with the solution of saturated NH4Cl aqueous solution/THF (1:1) (60.0 ml), the mixture was stirred at room temperature for 1 hour. Filter out the solid, extracted the mixture with CH$_2$Cl$_2$ (50 mL×2), the organic layer was dried over anhydrous MgSO$_4$, filtered and volatiles were removed under reduced pressure. The compound was isolated by column chromatography to give a light yellow solid 420 mg (84%). MH+ 460.3

N*3*-(3-Chloro-5-phenoxy-phenyl)-1,N*5*,N*5*-tris-(4-methoxy-benzyl)-1H-[1,2,4]triazole-3,5-diamine

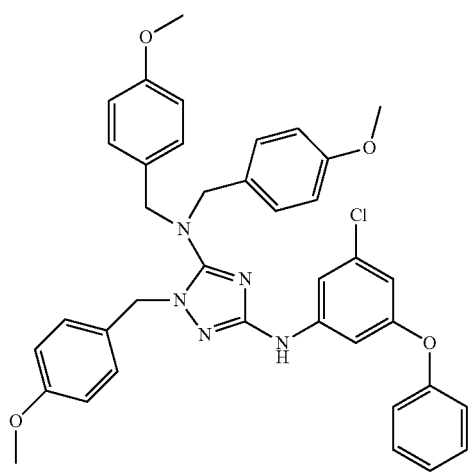 [SMILES: COc1ccc(CN(Cc2ccc(OC)cc2)c2nc(Nc3cc(Cl)cc(Oc4ccccc4)c3)nn2Cc2ccc(OC)cc2)cc1]

In a 25 mL sealed tube, sodium 2-methylpropan-2-olate (125 mg, 1.31 mmol, Eq: 1.20), bis(dibenzylideneacetone) palladium (62.6 mg, 109 μmol, Eq: 0.1) and 2-di-tert-butylphosphino-2',4',6'-triisopropylbiphenyl (46.2 mg, 109 μmol, Eq: 0.1) were combined with toluene (4.00 mL) to give a dark brown suspension. N5,N5,1-tris(4-methoxybenzyl)-1H-1,2,4-triazole-3,5-diamine (500 mg, 1.09 mmol, Eq: 1.00) and 1-bromo-3-chloro-5-phenoxybenzene (309 mg, 1.09 mmol, Eq: 1) were added. The reaction mixture was degassed with argon for 15 min, and then heated to 110° C. for 3 hours. The reaction mixture was cooled and diluted with EtOAc (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (Hexanes/EtOAc=70/30) to give an off-white solid 150 mg (21%). MH+ 662.4

N*3*-(3-Chloro-5-phenoxy-phenyl)-1H-[1,2,4]triazole-3,5-diamine (Compound 25)

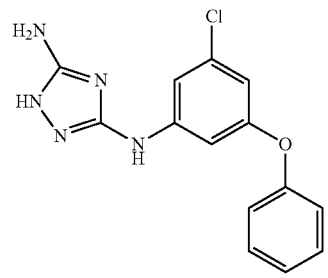 [SMILES: Nc1nc(Nc2cc(Cl)cc(Oc3ccccc3)c2)n[nH]1]

In 10 mL round bottle, N3-(3-chloro-5-phenoxyphenyl)-N5,N5,1-tris(4-methoxybenzyl)-1H-1,2,4-triazole-3,5-diamine (150 mg, 227 μmol, Eq: 1.00) was combined with TFA (5.00 mL) to give a colorless solution. The resulting solution was heated to 65° C. overnight, the reaction mixture was concentrated, and then diluted with EtOAc (30 mL). The solution was washed with saturated NaHCO$_3$, organic layer was dried over anhydrous MgSO$_4$, filtered and volatiles were removed under reduced pressure. The compound was isolated by preparative TLC to give an off-white solid 32 mg (47%). MH+ 302.0

Example 3

Procedure A

N*3*-[3,5-Dichloro-4-(pyridin-2-yloxy)-phenyl]-1H-[1,2,4]triazole-3,5-diamine (Compound 26)

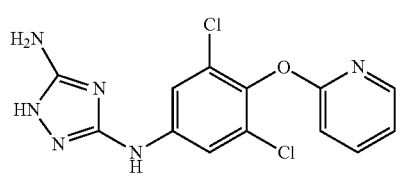

2-(2,6-Dichloro-4-nitro-phenoxy)-pyridine

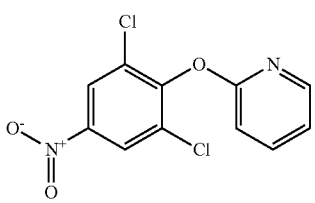 [SMILES: O=[N+]([O-])c1cc(Cl)c(Oc2ccccn2)c(Cl)c1]

In a 50 mL round-bottomed flask, potassium tert-butoxide (3.53 g, 31.5 mmol, Eq: 1.50) and pyridin-2(1H)-one (2 g, 21.0 mmol, Eq: 1.00) were combined with DMF (25.0 ml) to give a light brown suspension at 0° C. under nitrogen. 1,3-Dichloro-2-fluoro-5-nitrobenzene (4.42 g, 21.0 mmol, Eq: 1.00) was added. The reaction was stirred overnight at room temperature. The reaction mixture was diluted with $CH_2Cl_2$ (50 mL), washed with $H_2O$ (25 mL) and brine (25 mL) The organic layer was dried over anhydrous $MgSO_4$, filtered and volatiles were removed under reduced pressure to yield an oil from which the compound was isolated by column chromatography (Hexanes/EtOAc=70/30) to give an off-white solid 2.4 g (40%). MH+ 284.9

3,5-Dichloro-4-(pyridin-2-yloxy)-phenylamine

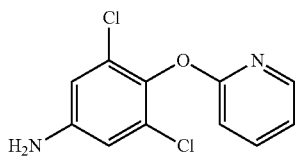 [SMILES: Nc1cc(Cl)c(Oc2ccccn2)c(Cl)c1]

In a 100 mL round bottle, 2-(2,6-dichloro-4-nitrophenoxy)pyridine (2.4 g, 8.42 mmol, Eq: 1.00) and zinc (2.75 g, 42.1 mmol, Eq: 5.00) were combined with a solution of saturated NH4Cl aqueous solution/THF (1:1) (50 ml), the mixture was stirred at for overnight. Filter out the solid, extracted with $CH_2Cl_2$ (50 mL×2), the organic layer was dried over anhydrous $Na_2SO_4$; the solution was concentrated under vacuum to afford the crude product 2.0 g (93%). MH+ 254.9

2-(2,6-Dichloro-4-isothiocyanato-phenoxy)-pyridine

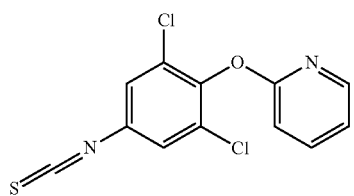 [SMILES: S=C=Nc1cc(Cl)c(Oc2ccccn2)c(Cl)c1]

In a 100 mL round-bottomed flask, di(1H-imidazol-1-yl) methanethione (2.1 g, 11.8 mmol, Eq: 1.5) was combined with $CH_2Cl_2$ (30 mL) to give a colorless solution. Di(1H-imidazol-1-yl)methanethione (2.1 g, 11.8 mmol, Eq: 1.5) in $CH_2Cl_2$ (20 mL) was added dropwise at 0° C. The reaction was allowed to warm to room temperature, and allowed to stir overnight. Concentrate the solution, the compound was isolated by column chromatography (Hexanes/EtOAc=80/20) to give the product 2.1 g (90%). MH+ 298.0

[3,5-Dichloro-4-(pyridin-2-yloxy)-phenylamino]-methylsulfanyl-methyl-cyanamide

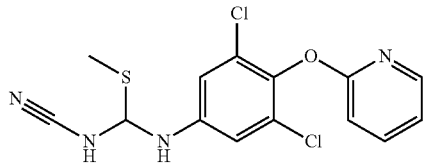 [SMILES: CSC(NC#N)Nc1cc(Cl)c(Oc2ccccn2)c(Cl)c1]

In a 100 mL round-bottomed flask, 2-(2,6-dichloro-4-isothiocyanatophenoxy)pyridine (1.2 g, 4.04 mmol, Eq: 1.00) in MeOH (20 mL), sodium hydrogencyanamide (292 mg, 4.56 mmol, Eq: 1.13) was added. The suspension turned to clear after a few minutes, the reaction was allowed to stir at room temperature for 1 hour, iodomethane (1.15 g, 8.08 mmol, Eq: 2) was added, the reaction mixture was allowed to stir at room temperature overnight. Concentrate the solution, the compound was isolated by column chromatography ($CH_2Cl_2$/MeOH=95/5) to give an off-white solid 1.2 g (84%). MH+ 352.9

N*3*-[3,5-Dichloro-4-(pyridin-2-yloxy)-phenyl]-1H-[1,2,4]triazole-3,5-diamine (Compound 26)

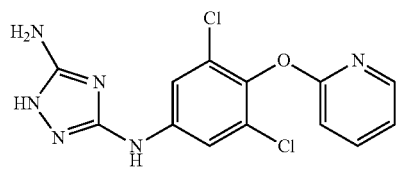

In a 100 mL round-bottomed flask, [3,5-dichloro-4-(pyridin-2-yloxy)-phenylamino]-methylsulfanyl-methyl-cyanamide (600 mg, 1.69 mmol, Eq: 1.00) in EtOH (30 mL), hydrazine (541 mg, 16.9 mmol, Eq: 10.00) was added. The reaction was heated to 65° C. for 3 hours. The reaction mixture was concentrated, added $H_2O$ (20 mL) to the residue, filtered out the solid and washed the solid with $H_2O$ (30 mL) and $CH_2Cl_2$ (10 mL), air-dried the solid overnight to give an off-white solid 382 mg (67%). MH+ 336.9

BIOLOGICAL EXAMPLES

Determination of Compounds HCV GT1b and GT1a Entry Inhibitory Activity Using the Pseudotyped HCV Particle (HCVpp) Reporter Assay Mammalian Expression Plasmids for the Generation of Pseudotyped Virus Particles:

Plasmids expressing HCV E1 and E2 envelope proteins of GT1a H77 strain (Proc Natl Acad Sci USA 1997 94:8738-43) or GT1b Con1 strain (Science 1999 285:110-3) were constructed by cloning the nucleic acids encoding the last 60 amino acids of HCV core protein and all of the HCV E1 and E2 proteins into pcDNA3.1(+) vector. Plasmid pVSV-G expressing the glycoprotein G of the vesicular stomatitis virus (VSV G) is from Clontech (cat #631530). The HIV packaging construct expressing the firefly luciferase reporter gene was modified based on the envelope defective pNL.4.3.Luc-R⁻.E⁻ vector (Virology 1995 206:935-44) by further deleting part of the HIV envelope protein.

Generation of Pseudotyped Virus Particles in Transiently Transfected HEK-293T Cells:

Pseudotyped HCV GT1a and GT1b particles (HCVpp) and the pseudotyped VSV G particles (VSVpp) were generated from transiently transfected HEK-293T cells (ATCC cat# CRL-573). For generating HCVpp, the HEK-293T cells were transfected with equal amounts of plasmids expressing the HCV envelope proteins and the HIV packaging genome by using polyethylenimine (Polysciences cat#23966) as transfection reagent. For generating VSVpp, the HEK-293T cells were transfected with equal amounts of plasmids expressing VSV G and the HIV packaging genome by using polyethylenimine. 24 hours after the transfection, the cell culture medium containing the transfection mixture was replaced with fresh Dulbecco's Modified Eagle Medium (DMEM-Glutamax™-I; Invitrogen cat #10569-010) supplemented with 10% Fetal Bovine Serum (Invitrogen cat #10082-147) and 2 mM L-glutamine (Invitrogen cat #25030-081). The supernatant was collected 48 hours after the transfection and filtered through a sterile 0.45 µm filter. Aliquots of the supernatant was frozen and stored at −80° C. until use.

Huh7-high CD81 cells with high CD81 expression level were enriched by flow cytometry sorting using FITC-labeled CD81 antibody JS-81 (BD Biosciences cat#561956) to allow more efficient HCV entry. The Huh7-high CD81 cells were cultured in Dulbecco's Modified Eagle Medium (DMEM-Glutamax™-I; Invitrogen cat #10569-010). The medium was supplemented with 10% Fetal Bovine Serum (Invitrogen cat #10082-147) and 1% penicillin/streptomycin (Invitrogen cat #15070-063). Cells were maintained at 37° C. in a humidified 5% $CO_2$ atmosphere.

Determination of Compound HCVpp Entry Inhibitory Activity in Huh7-High CD81 Cells Huh7-high CD81 cells were plated at a cell density of 8000 cells per well in 96 well plates (Perkin Elmer, cat #6005660). Cells were plated in 100 µl of Dulbecco's Modified Eagle Medium (DMEM-Glutamax™-I, Invitrogen Cat #10569-010) supplemented with 10% Fetal Bovine Serum (Invitrogen Cat #10082-147) and 1% penicillin/streptomycin (Invitrogen Cat #15070-063). Cells were allowed to equilibrate for 24 hours at 37° C. and 5% CO2 at which time compounds and pseudotyped viruses were added. On the day of the assay, HCVpp aliquots were thawed in 37° C. water bath and kept at 4° C. until use. Compounds (or medium as a control) were diluted in 3 fold dilution series in DMEM-Glutamax™-I with 2% DMSO and 2% penicillin/streptomycin. The 100 plating medium in each culture well was removed followed by the addition of 50 µl compound dilutions and 50 µl thawed HCVpp. Firefly luciferase reporter signal was read 72 hours after the addition of compounds and HCVpp using the Steady-Glo luciferase Assay System (Promega, cat # E2520) following the manufacturer's instruction. EC50 values were defined as the compound concentration at which a 50% reduction in the levels of firefly luciferase reporter was observed as compared to control samples in the absence of compound and was determined by non-linear fitting of compound dose-response data.

Determination of Compound Selectivity in Huh7-High CD81 Cells

Huh7 hCD81 cell assay plates and compound dilutions were set up in the same format as in the HCVpp assay. 24 hours after cell plating, thawed VSVpp was diluted by 800 fold in DMEM-Glutamax™-I supplemented with 10% fetal bovine serum. After removal of the cell plating medium from the culture wells, 50 µl compound dilutions and 50 µl diluted VSVpp were added to the wells. Firefly luciferase reporter signal was read 72 hours after the addition of compounds and VSVpp using the Steady-Glo luciferase Assay System (Promega, cat # E2520). EC50 values were defined as the compound concentration at which a 50% reduction in the levels of firefly luciferase reporter was observed as compared to control samples in the absence of compound and was determined by non-linear fitting of compound dose-response data. The EC50 was approximated if maximum percentage inhibition was less than 90% and more than 70%.

Representative assay data can be found in Table II below:

TABLE II

| Compound # | HCVpp GT-1a ($EC_{50}$, µM) | HCVpp GT-1b ($EC_{50}$, µM) | VSVpp ($EC_{50}$, µM) |
|---|---|---|---|
| 1 | 0.31 | | 13.2 |
| 2 | 2.439 | 0.393 | 86.0 |
| 3 | 2.774 | 0.329 | 35.5 |
| 4 | 0.076 | | 3.3 |
| 5 | 0.293 | | 25.3 |
| 6 | 0.139 | | 34.0 |
| 7 | | 0.009 | 100.0 |
| 8 | 0.114 | 0.079 | 10.0 |
| 9 | 0.15 | | 3.0 |
| 10 | 0.263 | | 7.7 |
| 11 | 0.61 | | 10.0 |
| 12 | 0.077 | | 3.4 |
| 13 | 0.674 | | 10.0 |
| 14 | 0.366 | | 10.0 |
| 15 | 0.133 | | 49.8 |
| 16 | 1.018 | | 40.2 |
| 17 | 1.036 | | 34.9 |
| 18 | 0.126 | | 0.1 |
| 19 | 0.019 | 0.008 | 20.2 |
| 20 | 0.232 | | 10.0 |
| 21 | 1.673 | | 39.2 |
| 22 | 1.645 | 0.229 | 14.3 |
| 23 | 4.623 | 0.517 | 40.1 |
| 24 | | 42.129 | 100.0 |
| 25 | | 1.899 | 100.0 |
| 26 | 1.878 | | 43.5 |

The foregoing invention has been described in some detail by way of illustration and example, for purposes of clarity and understanding. It will be obvious to one of skill in the art that changes and modifications may be practiced within the scope of the appended claims.

Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:
1. A compound selected from the group consisting of:
N5-(3-Fluoro-4-phenylsulfanyl-5-trifluoromethyl-phenyl)-1H-[1,2,4]triazole-3,5-diamine;
N3-(3-Chloro-4-phenylamino-phenyl)-1H-[1,2,4]triazole-3,5-diamine;
N3-(3-Chloro-4-phenoxy-phenyl)-1H-[1,2,4]triazole-3,5-diamine;
N3-(3,5-Dichloro-4-phenylsulfanyl-phenyl)-1H-[1,2,4]triazole-3,5-diamine;
N3-(4-Benzenesulfinyl-3,5-dichloro-phenyl)-1H-[1,2,4]triazole-3,5-diamine;
N3-(4-Benzenesulfinyl-3,5-dichloro-phenyl)-1H-[1,2,4]triazole-3,5-diamine;
N3-[3,5-Dichloro-4-(4-trifluoromethyl-phenylsulfanyl)-phenyl]-1H-[1,2,4]triazole-3,5-diamine;
N3-[3,5-Dichloro-4-(4-trifluoromethyl-benzenesulfinyl)-phenyl]-1H-[1,2,4]triazole-3,5-diamine;
N3-[3,5-Dichloro-4-(4-trifluoromethyl-benzenesulfinyl)-phenyl]-1H-[1,2,4]triazole-3,5-diamine;
$N^3$-[3,5-Dichloro-4-(2-trifluoromethyl-phenylsulfanyl)-phenyl]-1H-[1,2,4]triazole-3,5-diamine;
$N^3$-[3,5-Dichloro-4-(3-trifluoromethyl-benzenesulfinyl)-phenyl]-1H-[1,2,4]triazole-3,5-diamine;
4-[4-(5-Amino-1H-[1,2,4]triazol-3-ylamino)-2,6-dichloro-phenylsulfanyl]-benzonitrile;
4-[4-(5-Amino-1H-[1,2,4]triazol-3-ylamino)-2,6-dichloro-benzenesulfinyl]-benzonitrile;
4-[4-(5-Amino-1H-[1,2,4]triazol-3-ylamino)-2,6-dichloro-benzenesulfonyl]-benzonitrile;
4-[4-(5-Amino-1H-[1,2,4]triazol-3-ylamino)-2-chloro-6-trifluoromethyl-phenylsulfanyl]-benzoic acid methyl ester;
$N^3$-[3,5-Dichloro-4-(4-methoxy-phenylsulfanyl)-phenyl]-1H-[1,2,4]triazole-3,5-diamine;
$N^3$-[3-Chloro-4-(4-methoxy-phenylsulfanyl)-5-trifluoromethyl-phenyl]-1H-[1,2,4]triazole-3,5-diamine;
$N^3$-[3,5-Dichloro-4-(4-methoxy-benzenesulfonyl)-phenyl]-1H-[1,2,4]triazole-3,5-diamine;
$N^3$-[3,5-Dichloro-4-(4-methanesulfonyl-phenoxy)-phenyl]-1H-[1,2,4]triazole-3,5-diamine;
$N^3$-[3-Chloro-4-(4-methanesulfonyl-phenoxy)-5-trifluoromethyl-phenyl]-1H-[1,2,4]triazole-3,5-diamine;
$N^3$-(3-Chloro-4-phenylsulfanyl-phenyl)-1H-[1,2,4]triazole-3,5-diamine;
$N^3$-(4-Benzenesulfonyl-3-chloro-phenyl)-1H-[1,2,4]triazole-3,5-diamine;
$N^3$-(3-Chloro-4-phenylsulfanyl)-$N^3$-methyl-1H-[1,2,4]triazole-3,5-diamine;
$N^3$-(3-Chloro-5-phenoxy-phenyl)-1H-[1,2,4]triazole-3,5-diamine; and
$N^3$-[3,5-Dichloro-4-(pyridin-2-yloxy)-phenyl]-1H-[1,2,4]triazole-3,5-diamine.

* * * * *